(12) United States Patent
Lin et al.

(10) Patent No.: US 6,605,601 B2
(45) Date of Patent: Aug. 12, 2003

(54) A1 ADENOSINE RECEPTOR ANTAGONISTS

(75) Inventors: Ko-Chung Lin, Lexington, MA (US);
Chi Vu, Arlington, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/997,740

(22) Filed: Nov. 30, 2001

(65) Prior Publication Data

US 2002/0111333 A1 Aug. 15, 2002

Related U.S. Application Data

(60) Provisional application No. 60/250,658, filed on Dec. 1, 2000.

(51) Int. Cl.[7] .................... C07D 497/14; C07D 519/00; A61K 31/519; A61P 11/06; A61P 13/12

(52) U.S. Cl. .................... 514/81; 514/267; 544/244; 544/251

(58) Field of Search ................ 544/251, 244; 514/81, 267

(56) References Cited

U.S. PATENT DOCUMENTS 5,270,316 A * 12/1993 Suzuki et al. ............... 544/251

FOREIGN PATENT DOCUMENTS

| EP | 0 415 456 A | 3/1991 |
| EP | 0 423 805 A | 4/1991 |
| EP | 0 884 314 A | 12/1998 |
| WO | WO 98/57651 | 12/1998 |
| WO | WO 00/01388 | 1/2000 |

OTHER PUBLICATIONS

M. J. Dooley et al. "Theoretical Structure–Activity Studies of Adenosine A1 Ligands: Requirements for Receptor Affinity"*Bioorg. Med. Chem.*, 4(6), 1996, pp. 923–934.

* cited by examiner

*Primary Examiner*—Mark L. Berch
(74) *Attorney, Agent, or Firm*—Fish & Neave; James F. Haley, Jr.; Kristin M. Joslyn

(57) ABSTRACT

Compounds of Formula I and II are disclosed as antagonists of subtype A1 adenosine receptors. These compounds are useful for treatment of various diseases and disorders, including systemic hypertension, renal failure, diabetes, asthma, an edematous condition, congestive heart failure, and renal dysfunction.

FORMULA I

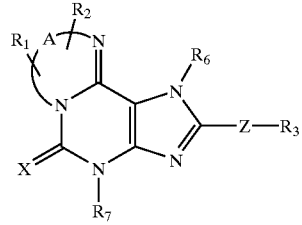

FORMULA II

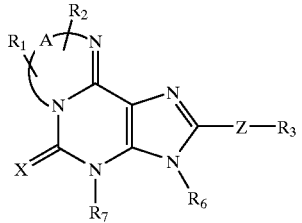

19 Claims, No Drawings

A1 ADENOSINE RECEPTOR ANTAGONISTS

This application claims benefit of U.S. Provisional Application No. 60/250,658, filed Dec. 1, 2000, which is herein incorporated by reference.

TECHNICAL FIELD OF THE INVENTION

This invention relates to medicinal chemistry and pharmacology. More particularly, it relates to antagonists of the adenosine receptors, pharmaceutical compositions comprising these compounds and methods of making and using the same in the treatment of diseases.

BACKGROUND OF THE INVENTION

Adenosine is a ubiquitous biochemical messenger. Adenosine binds to and activates seven-transmembrane spanning G-protein coupled receptors, eliciting a variety of physiological responses. Adenosine receptors are divided into four known subtypes (i.e., $A_1$, $A_{2a}$, $A_{2b}$, and $A_3$). These receptor subtypes mediate different, and sometimes opposing, effects. Activation of the adenosine $A_1$ receptor, for example, elicits an increase in renal vascular resistance, while activation of the adenosine $A_{2a}$ receptor elicits a decrease in renal vascular resistance.

In most mammalian organ systems, periods of metabolic stress result in significant increases in the concentration of adenosine in the tissue. The heart, for instance, produces and releases adenosine to mediate adaptive responses to stress, such as reductions in heart rate and coronary vasodilatation. Likewise, adenosine concentrations in kidneys increase in response to hypoxia, metabolic stress and many nephrotoxic substances. The kidneys also produce adenosine constitutively. The kidneys adjust the amount of constitutively produced adenosine in order to regulate glomerular filtration and electrolyte reabsorption. Regarding control of glomerular filtration, activation of $A_1$ receptors leads to constriction of afferent arterioles, while activation of $A_{2a}$ receptors leads to dilatation of efferent arterioles. Activation of $A_{2a}$ receptors exerts vasodilatory effects on the afferent arteriole. Overall, the effect of activation of these glomerular adenosine receptors is to reduce glomerular filtration rate. In addition, $A_1$ adenosine receptors are located in the proximal tubule and distal tubular sites. Activation of these receptors stimulates sodium reabsorption from the tubular lumen. Accordingly, blocking the effects of adenosine on these receptors produces a rise in glomerular filtration rate and an increase in sodium excretion.

SUMMARY OF THE INVENTION

The invention is based on the discovery that compounds of Formula I and II are potent and selective inhibitors of particular subtypes of adenosine receptors. Based on this discovery, the invention features adenosine antagonists useful in the prevention and/or treatment of numerous diseases, including cardiac and circulatory disorders, degenerative disorders of the central nervous system, respiratory disorders, and many diseases for which diuretic treatment is suitable. In general, the invention features highly potent and selective antagonists of the adenosine $A_1$ receptor.

The invention features compounds of formula I or II:

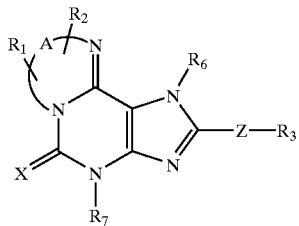

FORMULA I

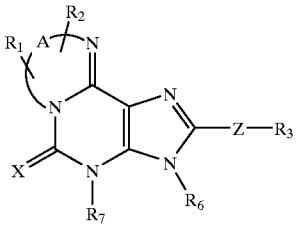

FORMULA II wherein $R_1$ and $R_2$ are independently selected from the group consisting of:
a) hydrogen;
b) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
c) aryl or substituted aryl;

$R_3$ is selected from the group consisting of:
(a) a bicyclic, tricyclic or pentacyclic group selected from the group consisting of:

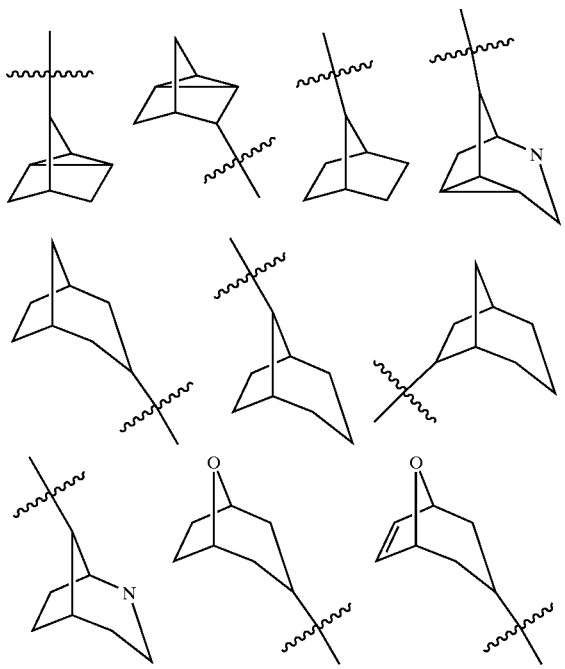

-continued

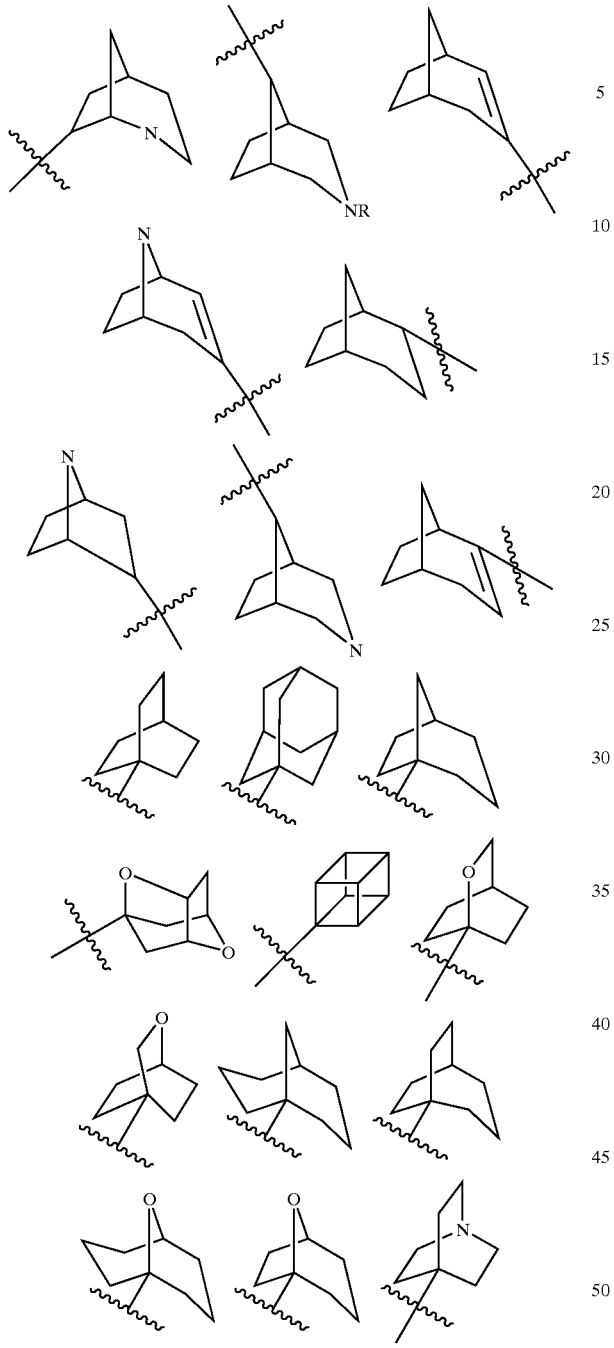

wherein the bicyclic, tricyclic or pentacyclic group is either unsubstituted or functionalized with one or more substituents selected from the group consisting of:
(i) alkyl, alkenyl and alkynyl; wherein each alkyl, alkenyl or alkynyl group is either unsubstituted or functionalized with one or more substituents selected from the group consisting of (alkoxycarbonyl)aralkylcarbamoyl, (amino)($R_5$) acylhydrazinylcarbonyl, (amino)($R_5$) acyloxycarboxy, (hydroxy)(carboalkoxy)alkylcarbamoyl, acylaminoalkylamino, acyloxy, aldehydo, alkenoxy, alkenylamino, alkenylsulfonylamino, alkoxy, alkoxycarbonyl, alkoxycarbonylalkylamino, alkoxycarbonylamino, alkoxycarbonylaminoacyloxy, alkoxycarbonylaminoalkylamino, alkylamino, alkylaminoalkylamino, alkylcarbamoyl, alkylphosphono, alkylsulfonylamino, alkylsulfonyloxy, amino, aminoacyloxy, aminoalkylaralkylcarbamoyl, aminoalkylcarbamoyl, aminoalkylheterocyclylalkylcarbamoyl, aminocycloalkylalkylcycloalkylcarbamoyl, aminocycloalkylcarbamoyl, aralkoxycarbonyl, aralkoxycarbonylamino, arylheterocyclyl, aryloxy, arylsulfonylamino, arylsulfonyloxy, carbamoyl, carbonyl, cyano, cyanoalkylcarbamoyl, cycloalkylamino, dialkylamino, dialkylaminoalkylamino, dialkylaminoalkylcarbamoyl, dialkylphosphono, haloalkylsulfonylamino, halogen, heterocyclyl, heterocyclylalkylamino, heterocyclylcarbamoyl, hydroxy, hydroxyalkylsulfonylamino, oximino, phosphate, phosphono, —$R_5$, $R_5$-alkoxy, $R_5$-alkyl (alkyl)amino, $R_5$-alkylalkylcarbamoyl, $R_5$-alkylamino, $R_5$-alkylcarbamoyl, $R_5$-alkylsulfonyl, $R_5$-alkylsulfonylamino, $R_5$-alkylthio, $R_5$-heterocyclylcarbonyl, substituted aralkylamino, substituted arylcarboxyalkoxycarbonyl, substituted arylsulfonylaminoalkylamino, substituted heteroarylsulfonylamino, substituted heterocyclyl, substituted heterocyclylaminoalkylamino, substituted heterocyclylsulfonylamino, sulfoxyacylamino, thiocarbamoyl, trifluoromethyl; and
(ii) (alkoxycarbonyl)aralkylcarbamoyl, (amino)($R_5$) acylhydrazinylcarbonyl, (amino)($R_5$) acyloxycarboxy, (hydroxy)(carboalkoxy) alkylcarbamoyl, acylaminoalkylamino, acyloxy, aldehydo, alkenoxy, alkenylamino, alkenylsulfonylamino, alkoxy, alkoxycarbonyl, alkoxycarbonylalkylamino, alkoxycarbonylamino, alkoxycarbonylaminoacyloxy, alkoxycarbonylaminoalkylamino, alkylamino, alkylaminoalkylamino, alkylcarbamoyl, alkylphosphono, alkylsulfonylamino, alkylsulfonyloxy, amino, aminoacyloxy, aminoalkylaralkylcarbamoyl, aminoalkylcarbamoyl, aminoalkylheterocyclylalkylcarbamoyl, aminocycloalkylalkylcycloalkylcarbamoyl, aminocycloalkylcarbamoyl, aralkoxycarbonyl, aralkoxycarbonylamino, arylheterocyclyl, aryloxy, arylsulfonylamino, arylsulfonyloxy, carbamoyl, carbonyl, cyano, cyanoalkylcarbamoyl, cycloalkylamino, dialkylamino, dialkylaminoalkylamino, dialkylaminoalkylcarbamoyl, dialkylphosphono, haloalkylsulfonylamino, halogen, heterocyclyl, heterocyclylalkylamino, heterocyclylcarbamoyl, hydroxy, hydroxyalkylsulfonylamino, oximino, phosphate, phosphono, —$R_5$, $R_5$-alkoxy, $R_5$-alkyl (alkyl)amino, $R_5$-alkylalkylcarbamoyl, $R_5$-alkylamino, $R_5$-alkylcarbamoyl, $R_5$-alkylsulfonyl, $R_5$-alkylsulfonylamino, $R_5$-alkylthio, $R_5$-heterocyclylcarbonyl, substituted aralkylamino, substituted arylcarboxyalkoxycarbonyl, substituted arylsulfonylaminoalkylamino, substituted heteroarylsulfonylamino, substituted heterocyclyl, substituted heterocyclyl-aminoalkylamino, substituted heterocyclyl-sulfonylamino, sulfoxyacylamino, thiocarbamoyl, trifluoromethyl;

$R_4$ is selected from the group consisting of hydrogen, $C_{1-4}$-alkyl, $C_{1-4}$-alkyl-$CO_2H$, and phenyl, wherein the $C_{1-4}$-alkyl, $C_{1-4}$-alkyl-$CO_2H$, and phenyl groups are either unsubstituted or functionalized with one to three substituents selected from the group consisting of halogen, —OH, —OMe, —$NH_2$, $NO_2$, benzyl, and benzyl functionalized with one to three substituents selected from the group consisting of halogen, —OH, —OMe, —$NH_2$, and —$NO_2$;

$R_5$ is selected from the group consisting of —$(CR_1R_2)_n$COOH, —$C(CF_3)_2OH$, —$CONHNHSO_2CF_3$, —$CONHOR_4$, —$CONHSO_2R_4$, —$CONHS_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR4$, —$OPO_3H_2$, —$OSO_3H$, —$PO(OH)R_4$, —$PO_3H_2$, —$SO_3H$, —$SO_2NHR_4$, —$SO_3NHCOR_4$, —$SO_3NHCONHCO_2R_4$, and the following:

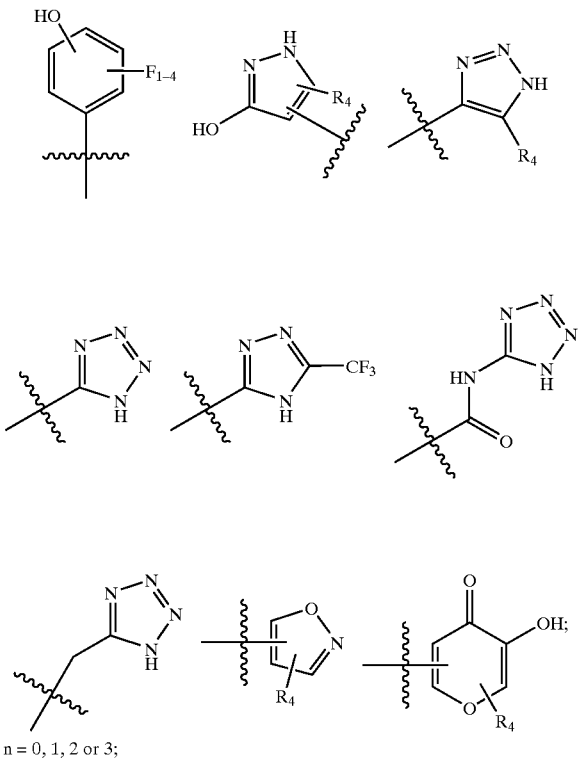

n = 0, 1, 2 or 3;

A is selected from the group consisting of —CH=CH, $(CH)_m$—$(CH)_{m'}$, CH=CH—$CH_2$, and —$CH_2$—CH=CH;

m=1 or 2;

X is O or S;

Z is selected from the group consisting of a single bond, —O—, —$(CH_2)_n$—, —$O(CH_2)_{1-2}$—, —$CH_2OCH_2$—, —$(CH_2)_{1-2}O$—, —CH=CHCH$_2$—, —CH=CH—, and —$CH_2$CH=CH—; and $R_6$ is selected from the group consisting of hydrogen, alkyl, acyl, alkylsufonyl, aralkyl, substituted aralkyl, substituted alkyl, and heterocyclyl; and $R_7$ is selected from the group consisting of:
a) hydrogen;
b) alkyl, alkenyl of not less than 3 carbons, or alkynyl of not less than 3 carbons; wherein said alkyl, alkenyl or alkynyl is either unsubstituted or functionalized with one or more substitutents selected from the group consisting of hydroxy, alkoxy, amino, alkylamino, dialkylamino, heterocyclyl, acylamino, alkylsulfonylamino, and heterocyclylcarbonylamino; and
c) aryl or substituted aryl;
d) alkylaryl or alkyl substituted aryl.

The compounds of Formula I or II optionally can be in forms such as an achiral compound, a racemate, an optically active compound, a pure diastereomer, a mixture of diastereomers, or a pharmacologically acceptable addition salt. In certain preferred embodiments, the compounds of the invention are compounds of Formula I or II wherein neither of $R_1$ and $R_2$ are hydrogen, that is, each of $R_1$ and $R_2$ are independently selected from the group consisting of a) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and b) aryl or substituted aryl.

More preferably, at least one of $R_1$ and $R_2$ is alkyl. In yet other preferred embodiments, A is —$(CH)_m$—$(CH)_{m'}$.

$R_7$ is alkyl in other preferred embodiments, and Z is preferably a single bond.

Preferred compounds of this invention are:

2-(4-Hydroxy-bicyclo[2.2.2]oct-1-yl)-7-isopropyl-4-propyl-1,4,6,7-tetrahydro-1,3,4,5a,8-pentaaza-as-indacen-5-one (compound 1);

7-Ethyl-2-(4-hydroxy-bicyclo[2.2.2]oct-1-yl)-4-propyl-1,4,6,7-tetrahydro-1,3,4,5a,8-pentaaza-as-indacen-5-one (compound 2);

3-[4-(7-Ethyl-5-oxo-4-propyl-4,5,6,7-tetrahydro-1H-1,3,4,5a,8-pentaaza-as-indacen-2-yl)-bicyclo[2.2.2]oct-1-yl]-propionic acid (compound 3);

2-(4-Hydroxy-bicyclo[2.2.2]oct-1-yl)-7-methyl-4-propyl-1,4,6,7-tetrahydro-1,3,4,5a,8-pentaaza-as-indacen-5-one (compound 4); and 3-[4-(7-Isopropyl-5-oxo-4-propyl-4,5,6,7-tetrahydro-1H-1,3,4,5a,8-pentaaza-as-indacen-2-yl)-bicyclo[2.2.2]oct-1-yl]-propionic acid (compound 5).

The compounds of this invention can be modified to enhance desired properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

The invention also features a pharmaceutical composition including any of the above compounds, alone or in a combination, together with a suitable excipient.

The invention also features a method of treating a patient displaying signs or symptoms of a disease or disorder wherein activation of A1 adenosine receptors plays a causative role in the disease or disorder. The method includes administering to the patient an effective amount of any of the above compounds. The disease or disorder can be, for example, systemic hypertension, renal failure, diabetes, asthma, an edematous condition, congestive heart failure, or renal dysfunction(e.g., renal dysfunction occurring as a side effect of a diuretic used to treat congestive heart failure, or renal toxicity occurring as a side effect of treatment with chemotherapeutic agents).

Compounds of the invention offer advantages, including the following. For example, (1) they can be used in low doses to minimize the likelihood of side effects and (2) they can be incorporated into numerous dosage forms including, but not limited to, pills, tablets, capsules, aerosols, suppositories, liquid formulations for ingestion or injection, dietary supplements, or topical preparations. In addition to human medical applications, the compounds of the invention can be used in the veterinary treatment of animals. In some embodiments, the pharmaceutical composition is formulated for oral, intravenous, intramuscular or subcutaneous administration.

This invention also feature a process for preparing the above compounds comprising the steps of: a) alkylating a thioketone to produce a thioether; b) reacting the thioether with a substituted amino alcohol to produce an alcohol intermediate; and c) cyclizing the alcohol intermediate to produce a cyclized product.

In some embodiments the above process further comprises the step of: a) converting the cyclized product to a carboxylic acid derivative. In some embodiments, the process comprises the steps of: a) coupling a diamino uracil with bicyclo[2.2.2]octane-1,4-dicarboxylic acid monomethyl ester to produce an acid; b) reducing the acid to a corresponding alcohol; c) oxidizing the alcohol to an aldehyde; d) coupling the aldehyde with methyl (triphenylphosphoroanylidene) acetate to produce a coupled product; e) converting the coupled product to a thioketone; f) alkylating the thioketone to produce a thioether; g) reacting the thioether with a substituted amino alcohol to produce an alcohol intermediate; and h) cyclizing the alcohol intermediate to produce a cyclized product; and i) converting the cyclized product to a carboxylic acid derivative.

In some embodiments, the process comprises the steps of a) coupling a diamino uracil with bicyclo[2.2.2]octane-1,4-dicarboxylic acid monomethyl ester to produce an acid; b) esterifying the acid to a corresponding ester; c) converting the ester to produce a thioketone; d) alkylating the thioketone to produce a thioether; e) reacting the thioether with a substituted amino alcohol to produce an alcohol intermediate; and f) cyclizing the alcohol intermediate to produce a cyclized product.and g) converting the cyclized product to a carboxylic acid derivative.

In some embodiments, the process comprises the steps of: a) nitrosating 6-amino-1-propyl-1H-pyrimidine-2,4-dione to produce a nitroso intermediate; b) reducing the nitroso intermediate to produce the corresponding diamino uracil; c) converting the diamino uracil to an amine salt; d) coupling the amine salt to 4-hydroxy-bicyclo[2.2.2]octane-1-carboxylic acid to produce a coupled product; and e) converting the coupled product to a thioketone; f) alkylating the thioketone to produce a thioether; g) reacting the thioether with a substituted amino alcohol to produce an alcohol intermediate; and h) cyclizing the alcohol intermediate to produce a cyclized product.

Other features and advantages of the invention will be apparent from the following detailed description, and from the claims.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Throughout this specification, the word "comprise" or variations such as "comprises" or "comprising" will be understood to imply the inclusion of a stated integer or groups of integers but not the exclusion of any other integer or group of integers.

As used herein, "alkenyl" group is an aliphatic carbon group that has at least one double bond. An alkenyl group can be straight or branched, and can have, for example, from 3 to 6 carbon atoms in a chain and 1 or 2 double bonds. Examples of alkenyl groups include, but are not limited to, allyl and isoprenyl.

As used herein, "alkynyl" group is an aliphatic carbon group that has at least one triple bond. An alkynyl group can be straight or branched, and can have, for example, from 3 to 6 carbon atoms in a chain and 1 to 2 triple bonds. Examples of alkynyl groups include, but are not limited to, propargyl and butynyl.

As used herein, "aryl" group is a phenyl or naphthyl group, or a derivative thereof. A "substituted aryl" group is an aryl group that is substituted with one or more substituents such as alkyl, alkoxy, amino, nitro, carboxy, carboalkoxy, cyano, alkylamino, dialkylamino, halo, hydroxy, hydroxyalkyl, mercaptyl, alkylmercaptyl, trihaloalkyl, carboxyalkyl, sulfoxy, or carbamoyl.

As used herein, "aralkyl" group is an alkyl group that is substituted with an aryl group. An example of an aralkyl group is benzyl.

As used herein, "cycloalkyl" group is an aliphatic ring of, for example, 3 to 8 carbon atoms. Examples of cycloalkyl groups include cyclopropyl and cyclohexyl.

As used herein, "acyl" group is a straight or branched alkyl-C(=O)— group or a formyl group. Examples of acyl groups include alkanoyl groups (e.g., having from 1 to 6 carbon atoms in the alkyl group). Acetyl and pivaloyl are examples of acyl groups. Acyl groups may be substituted or unsubstituted.

As used herein, "carbamoyl" group is a group having the structure $H_2N-CO_2-$. "Alkylcarbamoyl" and "dialkylcarbamoyl" refer to carbamoyl groups in which the nitrogen has one or two alkyl groups attached in place of the hydrogens, respectively. By analogy, "arylcarbamoyl" and "arylalkylcarbamoyl" groups include an aryl group in place of one of the hydrogens and, in the latter case, an alkyl group in place of the second hydrogen.

As used herein, "carboxyl" group is a —COOH group.

As used herein, "alkoxy" group is an alkyl-O— group in which "alkyl" is as previously described.

As used herein, "alkoxyalkyl" group is an alkyl group as previously described, with a hydrogen replaced by an alkoxy group, as previously described.

As used herein, "halogen" or "halo" group is fluorine, chlorine, bromine or iodine.

As used herein, "heterocyclyl" group is a 5 to about 10 membered ring structure, in which one or more of the atoms in the ring is an element other than carbon, e.g., N, O, S. A heterocyclyl group can be aromatic or non-aromatic, i.e., can be saturated, or can be partially or fully unsaturated. Examples of heterocyclyl groups include pyridyl, imidazolyl, furanyl, thienyl, thiazolyl, tetrahydrofuranyl, tetrahydropyranyl, morpholinyl, thiomorpholinyl, indolyl, indolinyl, isoindolinyl, piperidinyl, pyrimidinyl, piperazinyl, isoxazolyl, isoxazolidinyl, tetrazolyl, and benzimidazolyl.

As used herein, "substituted heterocyclyl" group is a heterocyclyl group wherein one or more hydrogens are replaced by substituents such as alkoxy, alkylamino, dialkylamino, carbalkoxy, carbamoyl, cyano, halo, trihalomethyl, hydroxy, carbonyl, thiocarbonyl, hydroxyalkyl or nitro.

As used herein, "hydroxyalkyl" means an alkyl group substituted by a hydroxy group.

As used herein, "sulfamoyl" group has the structure —S(O)$_2$NH$_2$. "Alkylsulfamoyl" and "dialkylsulfamoyl" refer to sulfamoyl groups in which the nitrogen has one or two alkyl groups attached in place of the hydrogens, respectively. By analogy, "arylsulfamoyl" and "arylalkylsulfamoyl" groups include an aryl group in place of one of the hydrogens and, in the latter case, an alkyl group in place of the second hydrogen.

As used herein, an "antagonist" is a molecule that binds to a receptor without activating the receptor. It competes with the endogenous ligand for this binding site and, thus, reduces the ability of the endogenous ligand to stimulate the receptor.

In the context of the present invention, a "selective antagonist" is an antagonist that binds to a specific subtype of adenosine receptor with higher affinity than to other adenosine receptor subtypes. The antagonists of the invention can, for example, have high affinity for A$_1$ receptors and are selective, having (a) nanomolar binding affinity for the A$_1$ receptor and (b) at least 10 times, more preferably 50 times, and most preferably at least 100 times, greater affinity for the A$_1$ receptor subtype than for any other receptor subtype.

As used herein, "pharmaceutically effective amount" means an amount effective in treating or preventing a condition characterized by an elevated adenosine concentration and/or increased sensitivity to adenosine. As used herein, the term "patient" means a mammal, including a human.

As used herein, "pharmaceutically acceptable carrier or adjuvant" means a non-toxic carrier or adjuvant that may be administered to an animal, together with a compound of this invention, and which does not destroy the pharmacological activity thereof.

In general, the invention relates to potent and selective antagonists of the adenosine A$_1$ receptor. Exemplary compounds of the invention are described in Table 1. The compounds taught herein exhibit IC50's against the Rat A1 receptor in the range of from about 7 to about 1095.

Synthesis of the Adenosine Antagonist Compounds

The compounds of the invention may be prepared by a number of known methods. For example, these compounds can be prepared by methods taught in Suzuki, F. et al. *J. Med. Chem.* 1992, 35, 3581–3583., and/or Shimada, J.; Suzuki, F. *Tetrahedron Lett.* 1992, 33, 3151–3154.

Three general synthetic schemes for producing the compounds of this invention are described below.

General Scheme for Method 1

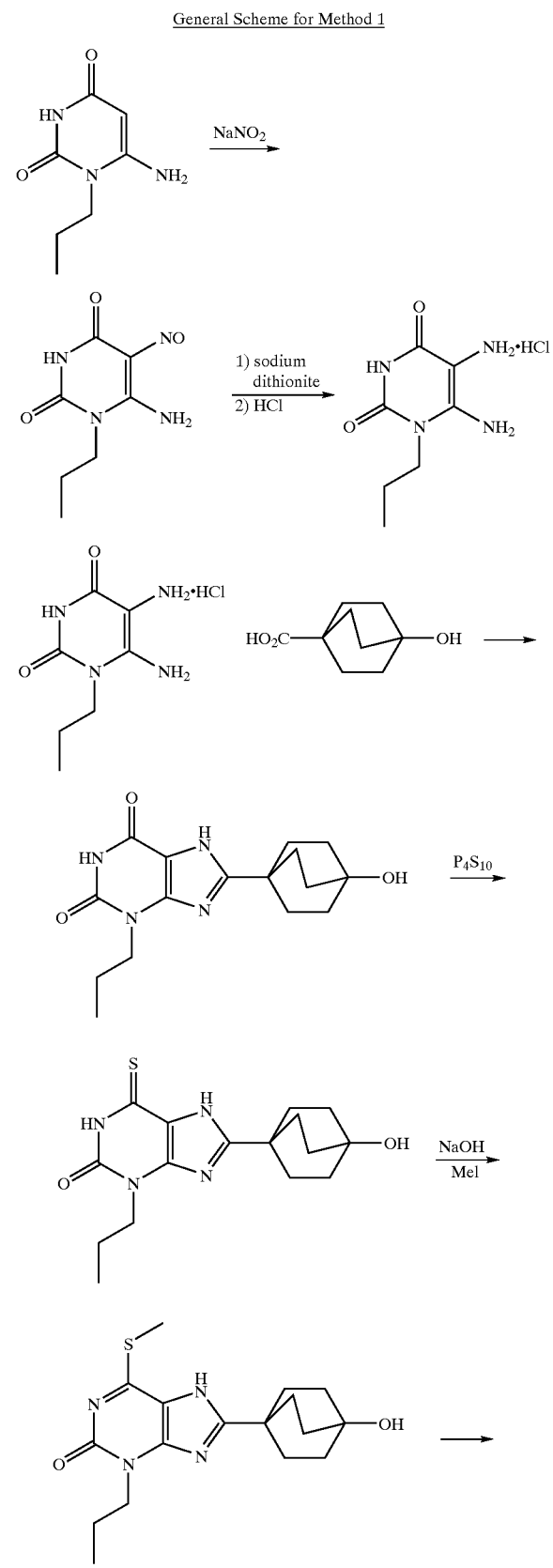

11
-continued
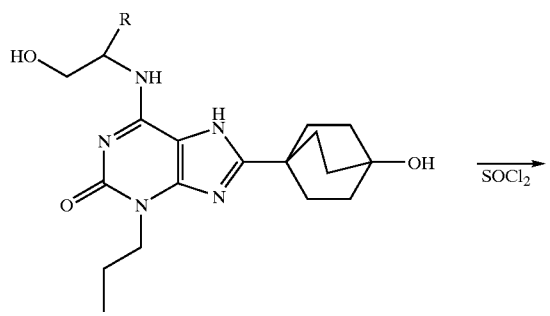
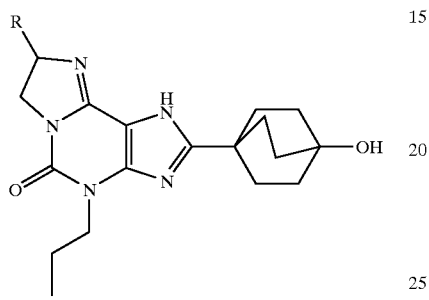
12
-continued
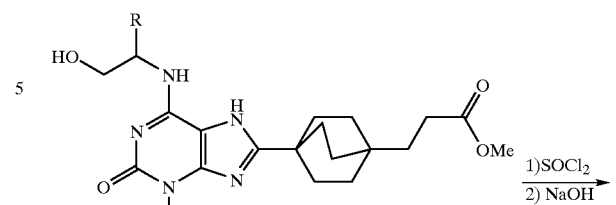
General Scheme for Method 3
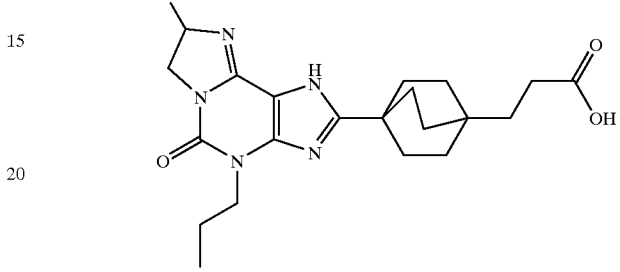
General Scheme for Method 2
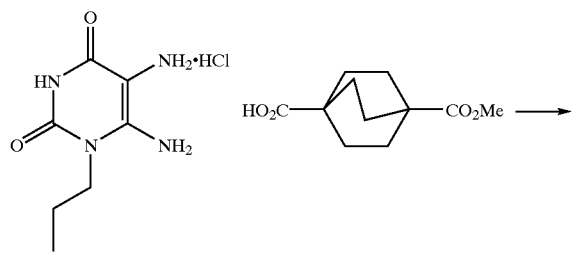
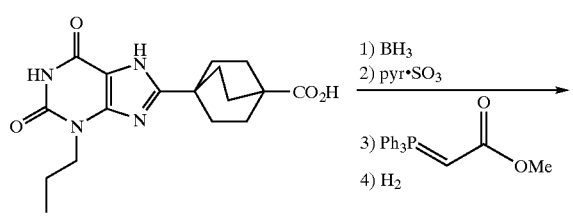
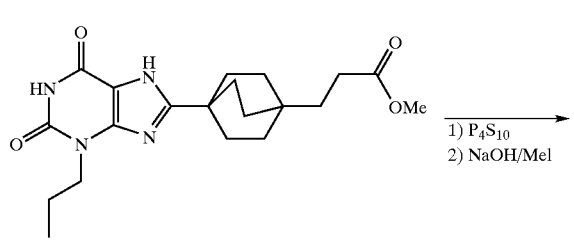
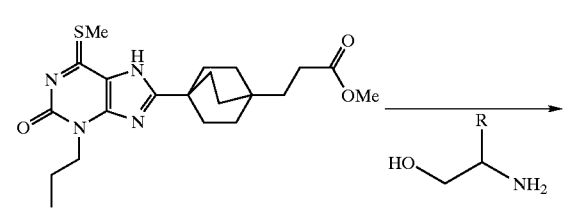
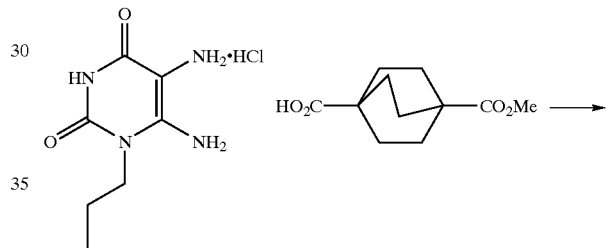
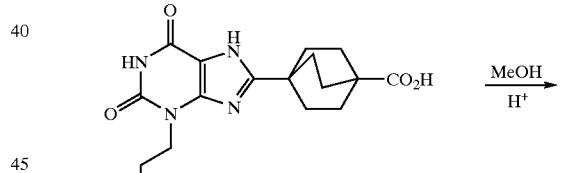
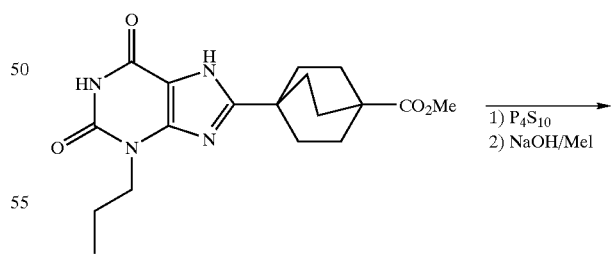
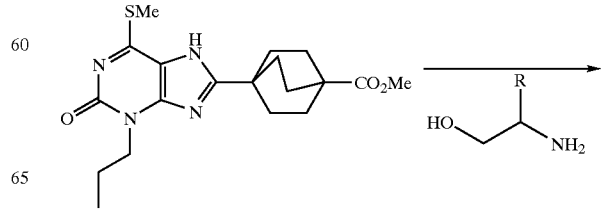

-continued

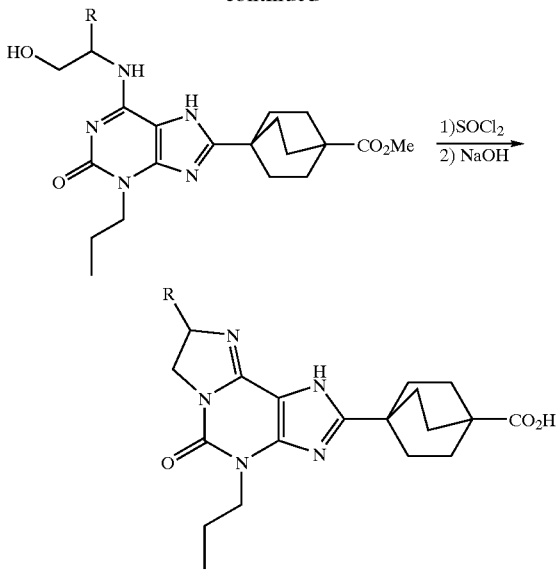

As can be appreciated by the skilled artisan, the above synthetic schemes are not intended to comprise a comprehensive list of all means by which the compounds described and claimed in this application may be synthesized. Further methods will be evident to those of ordinary skill in the art.

Uses for the Adenosine Antagonist Compounds

Activation of subtype A1 adenosine receptors elicits many physiological responses, including reductions in renal blood flow, reductions in glomerular filtration rate, and increases in sodium reabsorption in kidney. Activation of A1 adenosine receptors also reduces heart rate, reduces conduction velocity, and reduces contractility. These, and the other effects of activation of A1 adenosine receptors in other organs, are normal regulatory processes. However, these effects become pathological in many disease states. Thus, A1 adeno sine receptor antagonists have extensive application in both prevention and treatment of disease. Diseases that can be prevented and/or treated with A1 adenosine receptor antagonists include diseases and disorders wherein activation of A1 adenosine receptors plays a role in pathophysiology. Examples of such diseases and disorders include, but are not limited to, congestive heart failure,; respiratory disorders (e.g., bronchial asthma, allergic lung diseases); and many diseases for which diuretic treatment is indicated (e.g., acute and chronic renal failure, renal insufficiency, hypertension).

Additionally, the invention provides for the administration of highly selective and potent adenosine A1 receptor antagonists, for example, to elicit a diuretic response when administered alone and to potentiate the diuretic response to traditional diuretics. In addition, administration of A1 adenosine receptor antagonists with traditional diuretics attenuates the reduction of glomerular filtration rate induced by traditional diuretics. This is useful, for example, in treating edematous conditions, such as congestive heart failure and ascites.

Administration of the Adenosine Antagonist Compounds

The compounds can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird). The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Optionally, the compounds can be administered in conjunction with a non-adenosine modifying pharmaceutical composition (e.g., in combination with a non-adenosine modifying diuretic as described, for example, in co-pending application PCT/US99/08879 filed Apr. 23, 1999).

Pharmaceutical Compositions

The $A_1$ adenosine receptor antagonists may be formulated into pharmaceutical compositions for administration to animals, including humans. These pharmaceutical compositions, preferably include an amount of $A_1$ adenosine receptor antagonist effective to reduce vasoconstriction or enhance pulmonary hemodynamics and a pharmaceutically acceptable carrier.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of $A_1$ adenosine receptor antagonist that may be combined with the carrier materials to produce a single dosage form will vary depending upon the host treated and the particular mode of administration. The compositions can be formulated so that a dosage of between 0.01–100 mg/kg body weight of the $A_1$ adenosine receptor antagonist is administered to a patient receiving these compositions. In some ebodiments of the invention, the dosage is 0.1–10 mg/kg body weight. The composition may be administered as a single dose, multiple doses or over an established period of time in an infusion.

A specific dosage and treatment regimen for any particular patient will depend upon a variety of factors, including the particular $A_1$ adenosine receptor antagonist, the patient's age, body weight, general health, sex, and diet, and the time of administration, rate of excretion, drug combination, and the severity of the particular disease being treated. Judgment of such factors by medical caregivers is within ordinary skill in the art. The amount of antagonist will also depend on the individual patient to be treated, the route of administration, the type of formulation, the characteristics of the compound used, the severity of the disease, and the desired effect. The amounts of antagonists can be determined by pharmacological and pharmacokinetic principles well-known in the art.

In order that the invention described herein may be more fully understood, the following examples are set forth. It should be understood that these examples are for illustrative purposes only and are not to be construed as limiting this invention in any manner.

EXAMPLES

Example 1

Compounds 1, 2, 4, 8, 9, 11, 12–21, 24, 27, 28, 31 and 32 were prepared according to the following method using the appropriate amino alcohol in step 5. The amino alcohols used to prepare the compounds were: (R)-2-amino-3-methyl-1-butanol (compound 1); (R)-2-amino-1-butanol (compound 2); (R)-2-amino-1-propanol (compound 4); (R)-isoleucinol (compound 8); (R)-2-amino-1-butanol (compound 9); (R)-2-amino-1-pentanol (compound 11); (S)-1-amino-2-propanol (compound 12); (R)-2-amino-2-phenethanol (compound 13); (R)-1-amino-2-propanol (compound 14); (S)-isoleucinol (compound 15); (R)-2-amino-3,3-dimethyl-butan-1-ol (compound 16); (R)-2-amino-4-methyl-pentan-1-ol (compound 17); (R)-2-amino-3-phenyl-propan-1-ol (compound 18); (R)-2-amino-hexan-1-ol (compound 19); 3-aminopropanol (compound 20); 2-aminoethanol (compound 21); (S)-2-amino-1-butanol (compound 24) 4-aminobutanol (compound 27); (R)-4-(2-amino-3-hydroxy-propyl)-phenol (compound 28); (R)-3-amino-butan-1-ol (compound 31); and (R)-3-amino-pentan-1-ol (compound 32).

Table 1 depicts the structures of the compounds that were synthesized, the method used to synthesize the compounds and the mass spectrometry data for the compounds.

Step 1: 5,6-Diamino-1-propyl-1H-pyrimidine-2,4-dione hydrochloride salt

The starting material, 6-amino-1-propyl-1H-pyrimidine-2,4-dione, was prepared according to a known literature procedure (*J. Med. Chem.* 1989, p.1231). This material (8.5 g, 50 mmol) was dissolved in 250 mL of aqueous acetic acid and then cooled in an ice bath. Sodium nitrite (4.14 g,.1.2 eq) was added as a solution in 10 mL of water over a period of about 15 min. After about 10 min, a light red solid began to precipitate out of the reaction mixture. The solids were collected by filtration and dried under vacuum overnight to afford 8.0 g of the nitroso intermediate.

The nitroso intermediate (6.0 g, 30 mmol) was suspended in 100 mL of water and heated to 80–85° C. Sodium dithionite (15.8 g, 3.0 eq) was added fairly rapidly over a period of about 5 min. After about 5 min, the heating source was removed and the light green reaction mixture was cooled to rt and then in an ice bath. The solids were collected by filtration and dried under vacuum to afford the diamino uracil. This was then converted to the hydrochloride salt by dissolving in 10 mL of $H_2O$ containing 1.5 eq of HCl and then liophylized.

Step 2: 8-(4-Hydroxy-bicyclo[2.2.2]oct-1-yl)-3-propyl-3,7-dihydro-purine-2,6-dione 5,6-Diamino-1-propyl-1H-pyrimidine-2,4-dione hydrochloride salt (3.4 g) was dissolved in 80 mL of DMF along with 4-hydroxy-bicyclo[2.2.2]octane-1-carboxylic acid (2.5 g, 15 mmol). HATU (5.9 g, 1.05 eq) was added, followed by $Et_3N$ (8.30 mL, 4.05 eq). The resulting reaction mixture was stirred at rt overnight. The teaction mixture was filtered to remove some of the precipitate. The filtrate was concentrated under reduced pressure. The resulting residue was dissolved in 60 mL of $H_2O$ containing 10 eq of NaOH (5.9 g). The reaction mixture was stirred under reflux for 1 h, cooled to rt and acidified to pH2 with concentrated HCl. The resulting precipitate was collected by filtration and dried to afford 1.85 g of the xanthine derivative.

Step 3: 8-(4-Hydroxy-bicyclo[2.2.2]oct-1-yl)-3-propyl-6-thioxo-1,3,6,7-tetrahydro-purin-2-one 8-(4-Hydroxy-bicyclo[2.2.2]oct-1-yl)-3-propyl-3,7-dihydro-purine-2,6-dione (500 mg, 1.57 mmol) was dissolved in 10 mL of pyridine. $P_4S_{10}$ (1.05 g, 1.5 eq) was added and the reaction mixture was stirred under reflux for 6 h. The reaction mixture was then cooled to rt and quenched slowly with 5 mL of $H_2O$. The mixture was then acidified at 0° C. to pH 5 with 6 N HCl. The aqueous layer was extracted with EtOAc. The combined organic layer was dried ($Na_2SO_4$) and concentrated under reduced pressure. Purification by preparative HPLC afforded 100 mg of the titled compound.

Step 4: 8-(4-Hydroxy-bicyclo[2.2.2]oct-1-yl)-6-methylsulfanyl-3-propyl-3,7-dihydro-purin-2-one 8-(4-Hydroxy-bicyclo[2.2.2]oct-1-yl)-3-propyl-6-thioxo-1,3,6,7-tetrahydro-purin-2-one (120 mg, 0.36 mmol) was suspended in 3 mL of $H_2O$ and 1.5 mL of EtOH. NaOH was added as a solution in 0.4 mL of $H_2O$, followed by MeI. The reaction mixture was stirred at rt for 1 h. It was then neutralized with 0.1 N HCl and extracted with $CHCl_3$. The combined organic layers were dried ($Na_2SO_4$) and concentrated under reduced pressure to afford essentially quantitative amount of the titled compound.

Step 5: 8-(4-Hydroxy-bicyclo[2.2.2]oct-1-yl)-6-(1-hydroxymethyl-propylamino)-3-propyl-3,7-dihydro-purin-2-one 8-(4-Hydroxy-bicyclo[2.2.2]oct-1-yl)-6-methylsulfanyl-3-propyl-3,7-dihydro-purin-2-one (125 mg, 0.36 mmol) was dissolved in 3 mL of DMSO along with an excess of an appropriate amino alcohol (e.g., (R)-(–)-2-amino-1-butanol (0.24 mL, 7 eq) for compound 2). The resulting reaction mixture was stirred at 150° C. for 3 h. It was then cooled to rt and purified by preparative HPLC to afford 110 mg of the titled compound.

Step 6: 7-Ethyl-2-(4-hydroxy-bicyclo[2.2.2]oct-1-yl)-4-propyl-1,4,6,7-tetrahydro-1,3,4,5a,8-pentaaza-as-indacen-5-one (Compound 2)

8-(4-Hydroxy-bicyclo[2.2.2]oct-1-yl)-6-(1-hydroxymethyl-propylamino)-3-propyl-3,7-dihydro-purin-2-one (110 mg) was dissolved in 3 mL of $SOCl_2$ and stirred under reflux for 20 min. It was then cooled to rt and concentrated. The residue was quenched with saturated aq $NaHCO_3$ and extracted with $CHCl_3$. The combined organic layers were dried ($Na_2SO_4$) and concentrated under reduced pressure. Purification by preparative HPLC afforded 50 mg of the titled compound as the TFA salt.

Example 2

Compounds 3, 5 and 7 were prepared according to the following method using the appropriate amino alcohol in step 8. The amino alcohols used to prepare the compounds were: (R)-2-amino-1-butanol (compound 3); (R)-2-amino-3-methyl-1-butanol (compound 5); and (R)-2-amino-1-propanol (compound 7).

Table 1 depicts the structures of the compounds that were synthesized, the method used to synthesize the compounds and the mass spectrometry data for the compounds.

Step 1: 4-(2,6-Dioxo-3-propyl-2,3,6,7-tetrahydro-1H-purin-8-yl)-bicyclo[2.2.2]octane-1-carboxylic acid 5,6-Diamino-1-propyl-1H-pyrimidine-2,4-dione hydrochloride salt (570 mg) was dissolved in 20 mL of DMF along with bicyclo[2.2.2]octane-1,4-dicarboxylic acid monomethyl ester (520 mg, 2.45 mmol). HATU (980 mg, 1.05 eq) was added, followed by $Et_3N$ (1.40 mL, 4.05 eq). The resulting reaction mixture was stirred at rt overnight. The following morning, the reaction mixture was filtered to remove some of the precipitate. The filtrate was concentrated under reduced pressure. The resulting residue was dissolved in 10 mL of $H_2O$ containing 10 eq of NaOH (980 mg). The reaction mixture was stirred under reflux for 2 h. It was then cooled to rt and acidified to pH2 with concentrated HCl. The resulting precipitate was collected by filtration and dried to afford 680 mg of the acid derivative.

Step 2: 8-(4-Hydroxymethyl-bicyclo[2.2.2]oct-1-yl)-3-propyl-3,7-dihydro-purine-2,6-dione 4-(2,6-Dioxo-3-propyl-2,3,6,7-tetrahydro-1H-purin-8-yl)-bicyclo[2.2.2]octane-1-carboxylic acid (3.2 g, 9.25 mmol) was dissolved in 100 mL of anhydrous THF and cooled to 0° C. Borane-THF (1.0 M in THF, 18.5 mL, 2 eq) was added and the reaction mixture was stirred at 0° C. for 10 min, then warmed to rt and stirred for 48 h. The reaction mixture was then carefully quenched with 10 mL of MeOH and then concentrated under reduced pressure. The resulting residue was dissolved in 20 mL of MeOH and concentrated under reduced pressure. This treatment was repeated four more times to afford the desired alcohol.

Step 3: 4-(2,6-Dioxo-3-propyl-2,3,6,7-tetrahydro-1H-purin-8-yl)-bicyclo[2.2.2]octane-1-carbaldehyde 8-(4-Hydroxymethyl-bicyclo[2.2.2]oct-1-yl)-3-propyl-3,7-dihydro-purine-2,6-dione (2.70 g, 8.13 mmol) was dissolved in 40 mL of DMSO. Pyridine-$SO_3$ (3.88 g, 3 eq) was added, followed by $Et_3N$ (7.4 mL, 7 eq) at rt. The resulting reaction mixture was stirred at rt for 18 h. It was then diluted with EtOAc and washed with 5% aq citric acid, $H_2O$, brine, dried ($Na_2SO_4$) and concentrated under reduced pressure to afford 900 mg of the desired aldehyde.

Step 4: 3-[4-(2,6-Dioxo-3-propyl-2,3,6,7-tetrahydro-1H-purin-8-yl)-bicyclo[2.2.2]oct-1-yl]-acrylic acid methyl ester 4-(2,6-Dioxo-3-propyl-2,3,6,7-tetrahydro-1H-purin-8-yl)-bicyclo[2.2.2]octane-1-carbaldehyde (900 mg, 2.73 mmol) was dissolved in 25 mL of THF and methyl (triphenylphosphoranylidene)acetate (1.83 g, 2 eq) was added. The resulting reaction mixture was stirred under reflux for 18 h. It was then cooled to rt and purified by preparative HPLC using a mixture of aqueous acetonitrile to afford 300 mg of the desired product.

Step 5: 3-[4-(2,6-Dioxo-3-propyl-2,3,6,7-tetrahydro-1H-purin-8-yl)-bicyclo[2.2.2]oct-1-yl]-propionic acid methyl ester 3-[4-(2,6-Dioxo-3-propyl-2,3,6,7-tetrahydro-1H-purin-8-yl)-bicyclo[2.2.2]oct-1-yl]-acrylic acid methyl ester (300 mg) was dissolved in 20 mL of THF. 10%Pd on C (25 mg) was added and the resulting reaction mixture was hydrogenated under 50 psi of $H_2$ at rt for 6 h. The reaction mixture was filtered through Celite and the filtrate was concentrated under reduced pressure to afford 280 mg of the desired product.

Step 6: 3-[4-(2-Oxo-3-propyl-6-thioxo-2,3,6,7-tetrahydro-1H-purin-8-yl)-bicyclo[2.2.2]oct-1-yl]-propionic acid methyl ester 3-[4-(2,6-Dioxo-3-propyl-2,3,6,7-tetrahydro-1H-purin-8-yl)-bicyclo[2.2.2]oct-1-yl]-propionic acid methyl ester (250 mg, 0.64 mmol) was dissolved in 8 mL of pyridine. $P_4S_{10}$ (430 mg, 1.5 eq) was added and the reaction mixture was stirred under reflux for 3 h. It was then cooled to rt and quenched with 3 mL of $H_2O$ and then with enough 6 N HCl to bring the pH to 3. The resulting reaction mixture was extracted with $CHCl_3$. The organic layer was dried ($Na_2SO_4$) and concentrated under reduced pressure. The crude residue was purified by preparative HPLC to afford 100 mg of the desired product.

Step 7: 3-[4-(6-Methylsulfanyl-2-oxo-3-propyl-3,7-dihydro-2H-purin-8-yl)-bicyclo[2.2.2]oct-1-yl]-propionic acid methyl ester 3-[4-(2-Oxo-3-propyl-6-thioxo-2,3,6,7-tetrahydro-1H-purin-8-yl)-bicyclo[2.2.2]oct-1-yl]-propionic acid methyl ester (100 mg) was dissolved in 2 mL of EtOH and 1 mL of $H_2O$. NaOH (20 mg) was added as a solution in 1 mL of $H_2O$, followed by MeI (23 uL, 1.5 eq). The resulting reaction mixture was stirred at rt for 30 min. It was then extracted with EtOAc. The organic layer was dried ($Na_2SO_4$) and concentrated under reduced pressure to afford 105 mg of the titled compound.

Step 8: 3-{4-[6-(1-Hydroxymethyl-propylamino)-2-oxo-3-propyl-3,7-dihydro-2 H-purin-8-yl]-bicyclo [2.2.2]oct-1-yl}-propionic acid methyl ester 3-[4-(6-Methylsulfanyl-2-oxo-3-propyl-3,7-dihydro-2H-purin-8-yl)-bicyclo[2.2.2]oct-1-yl]-propionic acid methyl ester (105 mg) was dissolved in 2 mL of DMSO along with an appropriate amino alcohol (e.g., 160 uL of (R)-2-amino-1-butanol for compound 3). The reaction mixture was stirred at 150° C. for 3 h. It was then cooled to rt and purified by preparative HPLC to afford 50 mg of the titled compound.

Step 9: 3-[4-(7-Ethyl-5-oxo-4-propyl-4,5,6,7-tetrahydro-1H-1,3,4,5a,8-pentaaza-as-indacen-2-yl)-bicyclo[2.2.2]oct-1-yl]-propionic acid (compound 3)

3-{4-[6-(1-Hydroxymethyl-propylamino)-2-oxo-3-propyl-3,7-dihydro-2H-purin-8-yl]-bicyclo[2.2.2]oct-1-yl}-propionic acid methyl ester (30 mg) was dissolved in 1 mL of $SOCl_2$ and stirred under reflux for 15 min. The reaction mixture was then cooled to rt and concentrated under reduced pressure. The resulting residue was dissolved in a solution containing 1 mL of water, 0.5 mL of MeOH, and 0.1 mL of 10% aq. NaOH. The reaction mixture was stirred at rt for 30 min. It was then acidified to pH 2 with dilute 1 N HCl and concentrated. The resulting crude product was purified by preparative HPLC to afford the titled compound.

Example 3

Compounds 6, 10, 22, 23, 25, 26 29 and 30 were prepared according to the following method using the appropriate amino alcohol in step 3. The amino alcohols used to prepare the compounds were: 2-aminoethanol (compound 6); (R)-2-amino-1-butanol (compound 10); (R)-2-amino-1-propanol (compound 22); (R)-2-amino-1-pentanol (compound 23); (R)-isoleucinol (compound 25); (S)-2-amino-1-butanol (compound 26); 3-aminopropanol (compound 29); and 4-aminobutanol (compound 30). Table 1 depicts the structures of the compounds that were synthesized, the method used to synthesize the compounds and the mass spectrometry data for the compounds.

Step 1: 4-(2,6-Dioxo-3-propyl-2,3,6,7-tetrahydro-1H-purin-8-yl)-bicyclo[2.2.2]octane-1-carboxylic acid methyl ester 4-(2,6-Dioxo-3-propyl-2,3,6,7-tetrahydro-1H-purin-8-yl)-bicyclo[2.2.2]octane-1-carboxylic acid was prepared according to the procedure outlined above. This material (1.4 g) was suspended in 50 mL of MeOH and 5 drops of concentrated sulfuric acid was added. The reaction mixture was stirred under reflux for 18 h. It was then cooled to rt and concentrated under reduced pressure. The resulting residue was diluted with $CH_2Cl_2$ and washed with aq $NaHCO_3$, brine, dried ($Na_2SO_4$) and concentrated to afford 1.2 g of the titled compound.

Step 2: 4-(6-Methylsulfanyl-2-oxo-3-propyl-3,7-dihydro-2H-purin-8-yl)bicyclo[2.2.2]octane-1-carboxylic acid methyl ester 4-(2,6-Dioxo-3-propyl-2,3,6,7-tetrahydro-1H-purin-8-yl)-bicyclo[2.2.2]octane-1-carboxylic acid methyl ester (1.2 g, 3.33 mmol) was dissolved in 20 mL of pyridine. $P_4S_{10}$ (2.22 g, 1.5 eq) was added and the reaction mixture was stirred under reflux for 3 h. It was then cooled to 0° C. and carefully quenched with water. Enough 6 N HCl was added to bring the pH to 5 and the reaction mixture was extracted with $CH_2Cl_2$. The organic layer was dried ($Na_2SO_4$) and concentrated to afford 860 mg of the thio ester derivative. This material (860 mg, 2.29 mmol) was dissolved in 5 mL of EtOH and 5 mL of $H_2O$. NaOH (183 mg, 2 eq) was added as a solution in 2 mL of $H_2O$, followed by MeI (213 uL, 1.5 eq). The resulting reaction mixture was stirred at rt for 30 min. It was then extracted with EtOAc. The organic layer was dried ($Na_2SO_4$) and concentrated under reduced pressure to afford 800 mg of the titled compound.

Step 3: 4-(6-(2-Hydroxy-ethylamino)-2-oxo-3-propyl-3,7-dihydro-2H-purin-8-yl-bicyclo[2.2.2] octane-1-carboxylic acid methyl ester 4-(6-Methylsulfanyl-2-oxo-3-propyl-3,7-dihydro-2H-purin-8-yl)bicyclo[2.2.2]octane-1-carboxylic acid methyl ester (50 mg) was dissolved in 1 mL of 2 mL of DMSO along with an appropriate amino alcohol (e.g., 7 eq of 2-aminoethanol for compound 6). The reaction mixture was stirred at 150° C. for 3 h. It was then cooled to rt and purified by preparative HPLC to afford 30 mg of the titled compound.

Step 4: 4-(5-Oxo-4-propyl-4,5,6,7-tetrahydro-1H-1,3,4,5a,8-pentaaza-as-indacen-2-yl)-bicyclo[2.2.2]octane-l-carboxylic acid 4-[6-(2-Hydroxy-ethylamino)-2-oxo-3-propyl-3,7-dihydro-2H-purin-8-yl-bicyclo[2.2.2]octane-1-carboxylic acid methyl ester (30 mg) was dissolved in 1 mL of $SOCl_2$ and stirred under reflux for 15 min. The reaction mixture was then cooled to rt and concentrated under reduced pressure. The resulting residue was dissolved in a solution containing 1 mL of water, 0.5 mL of MeOH, and 0.1 mL of 10% aq. NaOH. The reaction mixture was stirred at rt for 30 min. It was then acidified to pH 2 with dilute 1 N HCl and concentrated. The resulting crude product was purified by preparative HPLC to afford the titled compound.

Example 4

Assay Methodology

Numerous xanthine derivatives were prepared, having the structures indicated in Table 1. For some of these compounds, the $K_i$ values for rat and human adenosine $A_1$ receptors were determined according to the following binding assay protocol.

Materials

Adenosine deaminase and HEPES were purchased from Sigma (St. Louis, Mo.). Ham's F-12 cell culture medium and fetal bovine serum were purchased from GIBCO Life Technologies (Gaithersburg, Md.). Antibiotic G-418, Falcon 150 mM culture plates and Costar 12-well culture plates were purchased from Fisher (Pittsburgh, Pa.). [$^3$H]CPX was purchased from DuPont-New England Nuclear Research Products (Boston, Mass.). Penicillin/streptomycin antibiotic mixture was purchased from Mediatech (Washington, DC). The composition of HEPES-buffered Hank's solution was: 130 mM NaCl, 5.0 mM Cl, 1.5 mM $CaCl_2$, 0.41 mM $MgSO_4$, 0.49 mM $Na_2HPO_4$, 0.44 mM $KH_2PO_4$, 5.6 m dextrose, and 5 mM HEPES (pH 7.4).

Membrane Preparation

Rat $A_1$ Receptor: Membranes were prepared from rat cerebral cortex isolated from freshly euthanized rats. Tissues were homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 min. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Human $A_1$ Receptor: Human A1 adenosine receptor cDNA was obtained by RT-PCR and subcloned into pcDNA3.1(Invitrogen). Stable transfection of CHO-K1 cells was performed using LIPOFECTAMINE-PLUS (GIBCO-BRL) and colonies were selected in 1 mg/ml G418, and screened using radioligand binding assays. For membrane preparations, CHO-K1 cells growing as monolayers in complete media (F12+10%FCS+1 mg/ml G418) were washed in PBS and harvested in buffer A supplemented with protease inhibitors. Cells were homogenized, centrifuged, and washed twice with buffer HE as described above. Final pellets were stored in aliquots at −80° C.

Radioligand Binding Assays

Membranes (50 μg membrane protein for rat A1ARs, and 25 μg of CHO-K1 membrane protein for human A1ARs), radioligands and varying concentrations of competing ligands were incubated in triplicates in 0.1 ml buffer HE plus 2 units/ml adenosine deaminase for 2.5 h at 21° C. Radioligand [$^3$H]DPCPX (112 Ci/mmol from NEN, final concentration: 1 nM) was used for competition binding assays on $A_1$ARs. Nonspecific binding was measured in the presence of 10 μM BG9719. Binding assays were terminated by filtration over Whatman GF/C glass fiber filters using a BRANDEL cell harvester. Filters were rinsed three times with 3–4 ml ice-cold 10 mM Tris-HCl, pH 7.4 and 5 mM $MgCl_2$ at 4° C. Filter paper was transferred to a vial, and 3 ml of scintillation cocktail ScintiVerseII (Fisher)was added. Radioactivity was counted in a Wallac β-counter.

Analysis of Binding Data

For $K_1$ Determinations: Competition binding data were fit to a single-site binding model and plotted using Prizm GraphPad. Cheng-Prusoff equation $K_1=IC_{50}/(1+[I]/K_D)$ was used to calculate $K_I$ values from $IC_{50}$ values, where $K_I$ is the affinity constant for the competing ligand, [I] is the concentration of the free radioligand, and $K_D$ is the affinity constant for the radioligand.

For % Binding: For one-point binding assays, data were presented as % of total specific binding at 1 μM of competing compound: % of total =100* (Specific binding with 1 μM of competing compound/total specific binding). % binding represents the amount of bound radioligand remaining in the presence of 1 μM of competing antagonist.

Results

All of the compounds tested exhibited rat $A_1$ $K_i$ values between about 4 and about 800 nM. In Table 2, the rat A1 adenosine receptor Ki value and % binding for the compounds are presented.

Example 5

Alternative Assay Methodology

Materials

See Example 4.

Cell Culture

CHO cells stably expressing the recombinant human $A_1$AdoR (CHO:$A_1$AdoR cells) were prepared as described (Kollias-Barker et al., *J. Pharma. Exp. Ther.* 281(2), 761, 1997) and cultured as for CHO:Wild cells. CHO cells were cultured as monolayers on plastic dishes in Ham's F-12 medium supplemented with 10% fetal bovine serum, 100 U penicillin G and 100 μg streptomycin in a humidified atmosphere of 5% $CO_2$/95% air at 37° C. The density of [$^3$H]CPX binding sites in CHO cells was 26±2 (n=4) fmol/mg protein. Cells were subcultured twice weekly after detachment using 1 mM EDTA in $Ca^{2+}$-$Mg^{2+}$-free HEPES-buffered Hank's solution. Three different clones of CHO:$A_1$AdoR cells were used for experiments, and all results were confirmed with cells from two or three clones. The density of $A_1$AdoRs in these cells was 4000–8000 fmol/mg protein, as determined by assay of [$^3$H]CPX specific binding.

Radioligand Binding

CHO cells grown on 150 mm culture dishes were rinsed with HEPES-buffered Hank's solution, then removed with a cell scraper and homogenized in ice-cold 50 mM Tris-HCl, pH 7.4. Cell membranes were pelleted by centrifugation of the cell homogenate at 48,000×g for 15 minutes. The membrane pellet was washed twice by resuspension in fresh buffer and centrifugation. The final pellet was resuspended in a small volume of 50 mM Tris-HCl, pH 7.4, and stored in aliquots of 1 ml at −80° C. until used for assays.

To determine the density of $A_1$AdoRs in CHO cell membranes, 100 μl aliquots of membranes (5 μg protein) were incubated for 2 hours at 25° C. with 0.15–20 nM [$^3$H]CPX and adenosine deaminase (2 U/ml) in 100 μl of 50 mM Tris-HCl, pH 7.4. Incubations were terminated by dilution with 4 ml of ice-cold 50 mM Tris-HCl buffer and immediate collection of membranes onto glass-fiber filters (Schleicher and Schuell, Keene, N.H.) by vacuum filtration (Brandel, Gaithersburg, Md.). Filters were washed quickly three times with ice-cold buffer to remove unbound radioligand. Filter discs containing trapped membranes bound radioligand were placed in 4 ml of Scintiverse BD (Fisher), and the radioactivity was quantified using a liquid scintillation counter. To determine nonspecific binding of [$^3$H] CPX, membranes were incubated as described above and 10 μM CPT was added to the incubation buffer. Nonspecific binding was defined as [$^3$H]CPX bound in the presence of 10 μM CPT. Specific binding of the radioligand to the $A_1$AdoR was determined by subtracting nonspecific binding from total binding. Nonspecific binding was found to increase linearly with an increase of [$^3$H]CPX concentration. Triplicate assays were done at each tested concentration of [$^3$H]CPX.

To determine the affinities of antagonists of $A_1$AdoRs for the human recombinant $A_1$AdoRs expressed in CHO cells, binding of 2 nM [$^3$H]CPX in the presence of increasing concentrations of antagonist was measured. Aliquots of CHO cell membranes (100 μl: 5 μg protein), [$^3$H]CPX, antagonist (0.1 nM-100 μM), and adenosine deaminase (2 U/ml) were incubated for 3 hours at 25° C. in 200 μl of 50 mM Tris-HCl buffer (pH 7.4). Assays were terminated as described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

| Compound | Structure | Synthetic Method | MS (M + 1) |
| --- | --- | --- | --- |
| 1 | 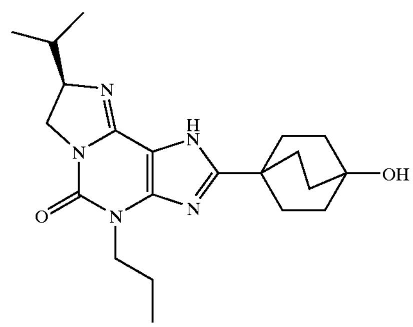 | 1 | 386 |
| 2 | 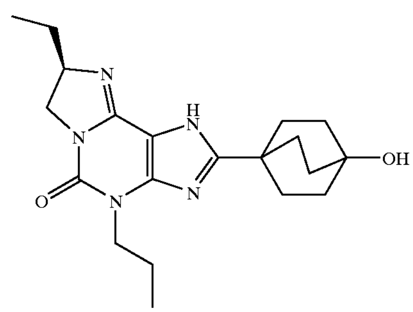 | 1 | 372 |
| 3 | 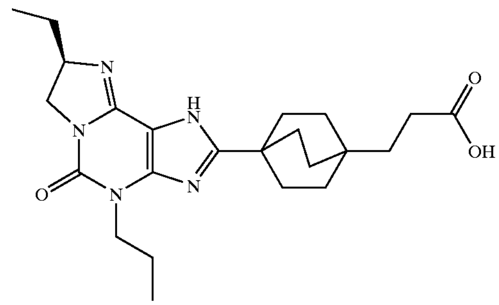 | 2 | 428 |

TABLE 1-continued

| Compound | Structure | Synthetic Method | MS (M + 1) |
|---|---|---|---|
| 4 | 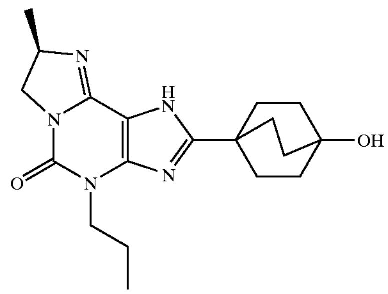 | 1 | 358 |
| 5 | 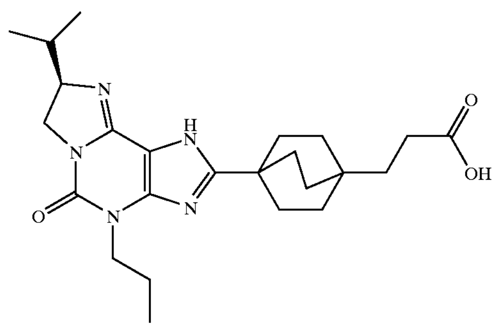 | 2 | 442 |
| 6 | 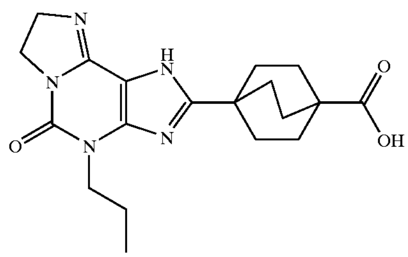 | 3 | 372 |
| 7 | 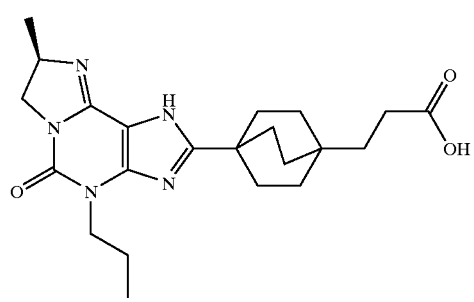 | 2 | 414 |
| 8 | 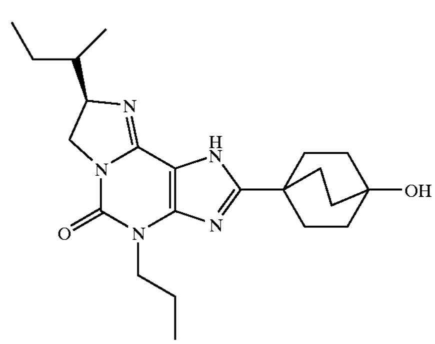 | 1 | 400 |

TABLE 1-continued

| Compound | Structure | Synthetic Method | MS (M + 1) |
|---|---|---|---|
| 9 | 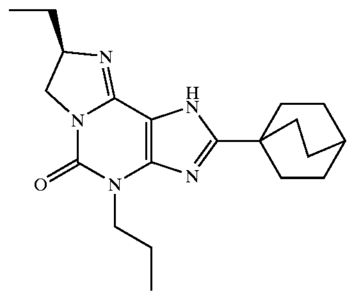 | 1 | 356 |
| 10 | 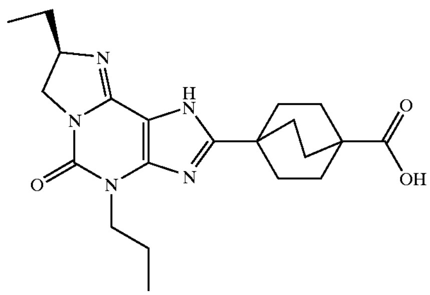 | 3 | 400 |
| 11 | 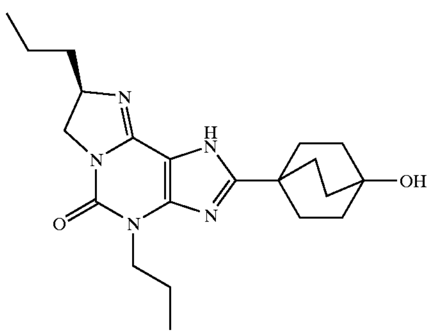 | 1 | 386 |
| 12 | 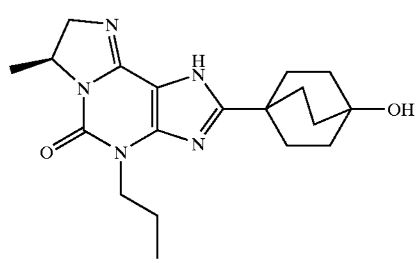 | 1 | 358 |
| 13 | 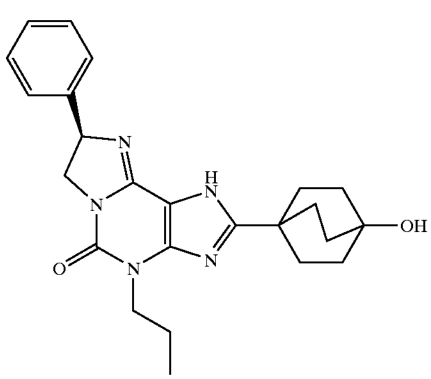 | 1 | 420 |

TABLE 1-continued

| Compound | Structure | Synthetic Method | MS (M + 1) |
|---|---|---|---|
| 14 | 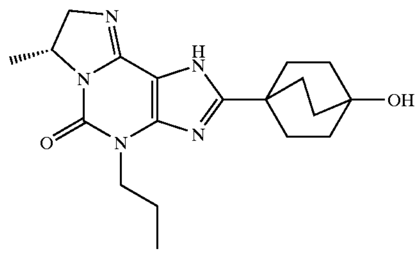 | 1 | 358 |
| 15 | 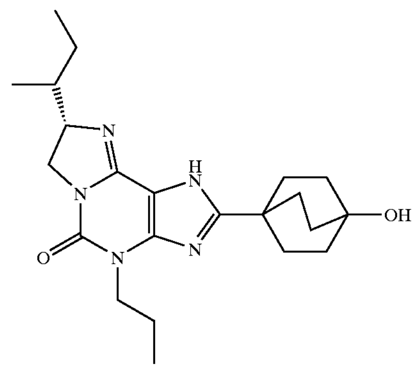 | 1 | 400 |
| 16 | 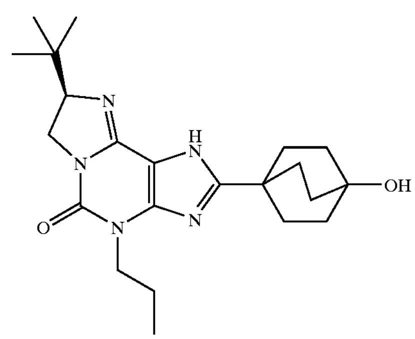 | 1 | 400 |
| 17 | 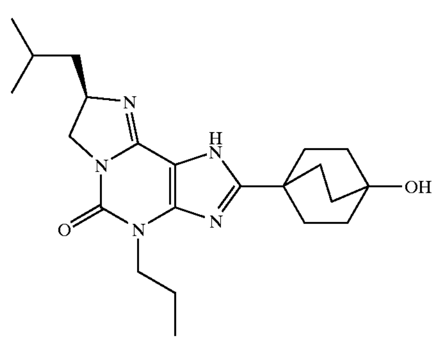 | 1 | 400 |

TABLE 1-continued

| Compound | Structure | Synthetic Method | MS (M + 1) |
|---|---|---|---|
| 18 | 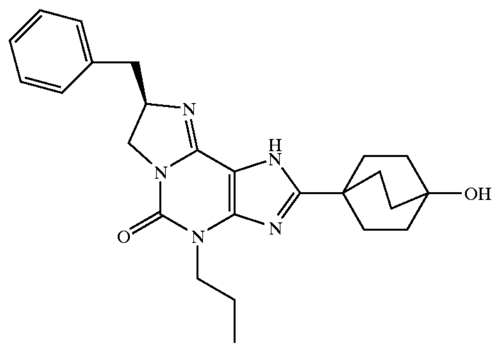 | 1 | 434 |
| 19 | 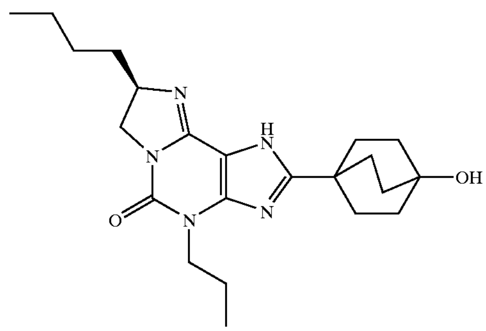 | 1 | 400 |
| 20 | 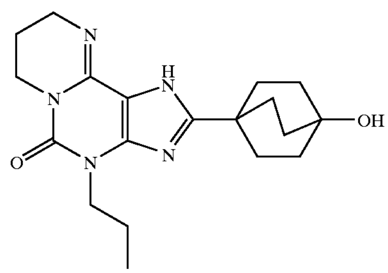 | 1 | 358 |
| 21 | 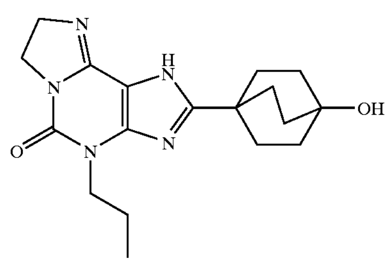 | 1 | 344 |
| 22 | 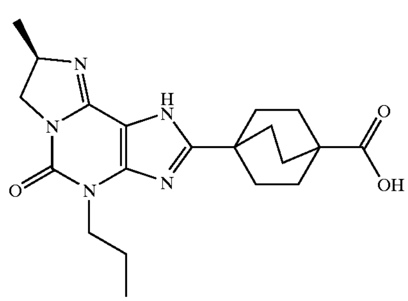 | 3 | 386 |

TABLE 1-continued
| Compound | Structure | Synthetic Method | MS (M + 1) |
|---|---|---|---|
| 23 | 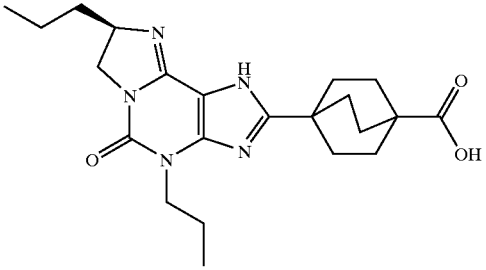 | 3 | 414 |
| 24 | 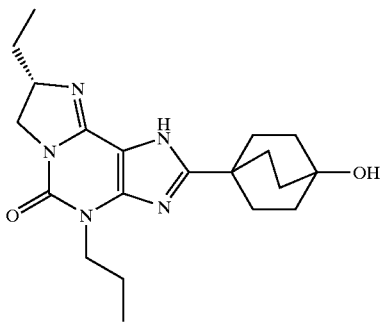 | 1 | 372 |
| 25 | 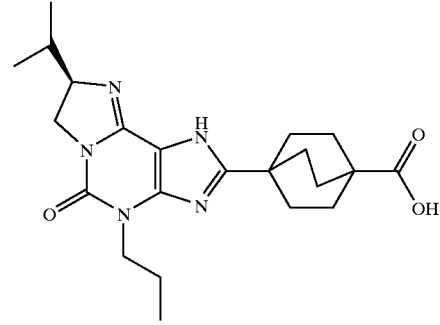 | 3 | 414 |
| 26 | 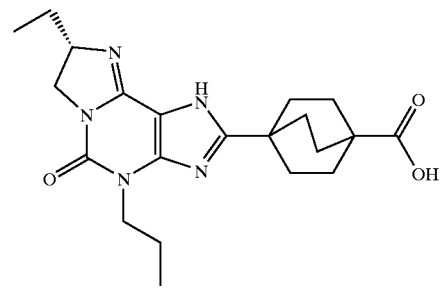 | 3 | 400 |
| 27 | 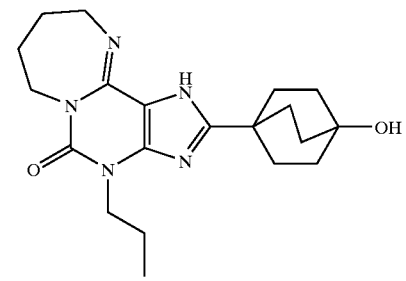 | 1 | 372 |

TABLE 1-continued
| Compound | Structure | Synthetic Method | MS (M + 1) |
|---|---|---|---|
| 28 | 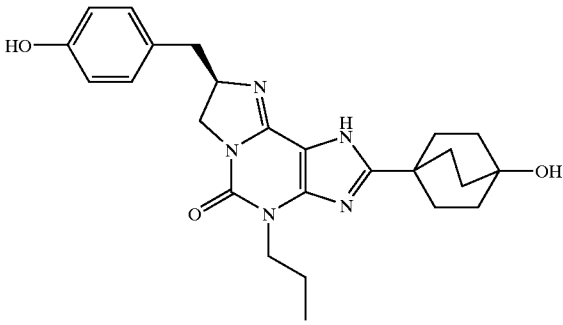 | 1 | 450 |
| 29 | 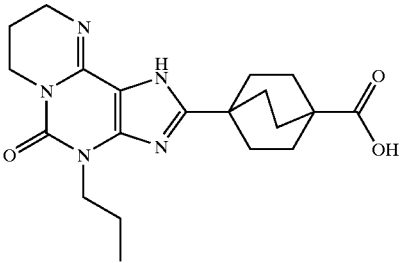 | 3 | 386 |
| 30 | 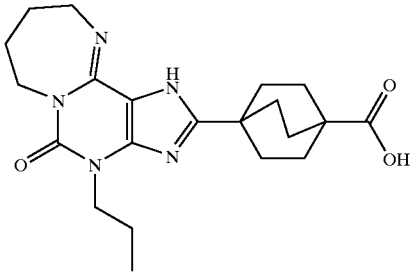 | 3 | 400 |
| 31 | 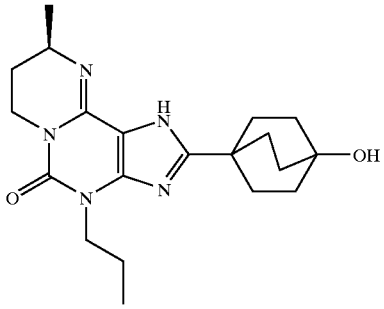 | 1 | 372 |
| 32 | 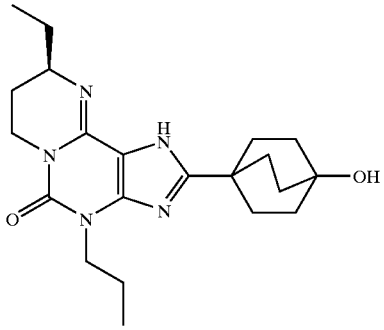 | 1 | 372 |

TABLE 2

| Compound No. | Ki (nM) | % Binding |
|---|---|---|
| 1 | 4.4 | ND |
| 2 | 5.75 | ND |
| 3 | 8.38 | ND |
| 4 | 9.92 | ND |
| 5 | 10.5 | 1.9 |
| 6 | ND | 2.6 |
| 7 | 13.7 | 2.5 |
| 8 | 14.1 | 1 |
| 9 | 26.7 | 0.1 |
| 10 | 40.2 | 6.2 |
| 11 | 43.2 | 3.7 |
| 12 | 51.3 | 8.6 |
| 13 | 68.3 | ND |
| 14 | 68.5 | 7.8 |
| 15 | 93 | 7.7 |
| 16 | 155 | ND |
| 17 | 166.7 | ND |
| 18 | 708 | ND |
| 19 | ND | 18.1 |
| 20 | ND | 52.7 |
| 21 | ND | 12.2 |
| 22 | ND | 24 |
| 23 | ND | 22.8 |
| 24 | ND | 11 |
| 25 | ND | 46.7 |
| 26 | ND | 41.1 |
| 27 | ND | 16.3 |
| 28 | ND | 36.3 |
| 29 | ND | 81.8 |
| 30 | ND | 71 |
| 31 | ND | 40 |
| 32 | ND | 61 |

What is claimed is:

1. A compound of formula I:

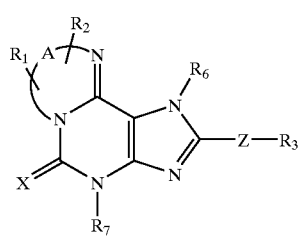

FORMULA I or a pharmacologically acceptable addition salt thereof
wherein $R_1$ and $R_2$ are independently selected from the group consisting of:
   a) hydrogen;
   b) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
   c) aryl or substituted aryl;
$R_3$ is a bicyclic, tricyclic or pentacyclic group selected from the group consisting of:

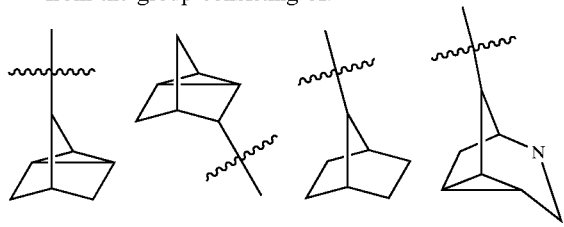

-continued

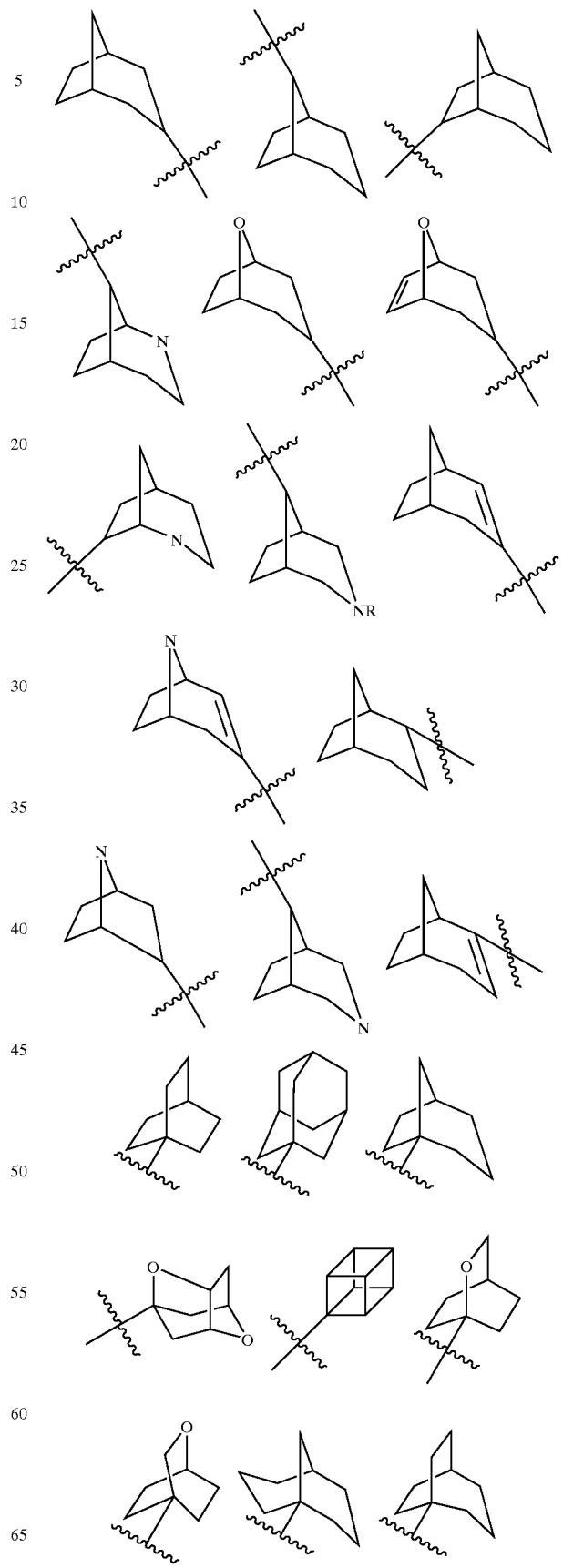

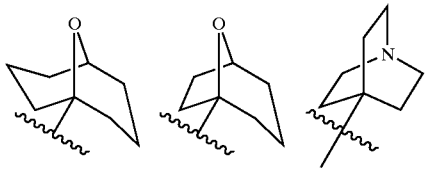

wherein the bicyclic, tricyclic or pentacyclic group is either unsubstituted or functionalized with one or more substituents selected from the group consisting of:

(i) alkyl, alkenyl and alkynyl; wherein each alkyl, alkenyl or alkynyl group is either unsubstituted or functionalized with one or more substituents selected from the group consisting of (alkoxycarbonyl)aralkylcarbamoyl, (amino)($R_5$)acylhydrazinylcarbonyl, (amino)($R_5$)acyloxycarboxy, (hydroxy)(carboalkoxy)alkylcarbamoyl, acyloxy, aldehydo, alkenoxy, alkenylamino, alkenylsulfonylamino, alkoxy, alkoxycarbonyl, alkoxycarbonylamino, alkoxycarbonylaminoacyloxy, alkylamino, alkylcarbamoyl, alkylphosphono, alkylsulfonylamino, alkylsulfonyloxy, amino, aminoacyloxy, aralkoxycarbonyl, aralkoxycarbonylamino, arylheterocyclyl, aryloxy, arylsulfonylamino, arylsulfonyloxy, carbamoyl, cyano, cycloalkylamino, dialkylamino, dialkylphosphono, haloalkylsulfonylamino, halogen, heterocyclyl, heterocyclylcarbamoyl, hydroxy, —$R_5$, $R_5$-alkoxy, $R_5$-alkyl(alkyl)amino, $R_5$-alkylamino, $R_5$-alkylsulfonyl, $R_5$-alkylsulfonylamino, $R_5$-alkylthio, $R_5$-heterocyclylcarbonyl, substituted aralkylamino, substituted arylcarboxyalkoxycarbonyl, substituted heteroarylsulfonylamino, substituted heterocyclyl, substituted heterocyclylsulfonylamino, sulfoxyacylamino, thiocarbamoyl, trifluoromethyl; and (ii) (alkoxycarbonyl)aralkylcarbamoyl, (amino)($R_5$)acylhydrazinylcarbonyl, (amino)($R_5$)acyloxycarboxy, (hydroxy)(carboalkoxy)alkylcarbamoyl, acyloxy, aldehydo, alkenoxy, alkenylamino, alkenylsulfonylamino, alkoxy, alkoxycarbonyl, alkoxycarbonylamino, alkoxycarbonylaminoacyloxy, alkylamino, alkylcarbamoyl, alkylphosphono, alkylsulfonylamino, alkylsulfonyloxy, amino, aminoacyloxy, aralkoxycarbonyl, aralkoxycarbonylamino, arylheterocyclyl, aryloxy, arylsulfonylamino, arylsulfonyloxy, carbamoyl, cyano, cycloalkylamino, dialkylamino, dialkylphosphono, haloalkylsulfonylamino, halogen, heterocyclyl, heterocyclylcarbamoyl, hydroxy, —$R_5$, $R_5$-alkoxy, $R_5$-alkyl(alkyl)amino, $R_5$-alkylamino, $R_5$-alkylsulfonyl, $R_5$-alkylsulfonylamino, $R_5$-alkylthio, $R_5$-heterocyclylcarbonyl, substituted aralkylamino, substituted arylcarboxyalkoxycarbonyl, substituted heteroarylsulfonylamino, substituted heterocyclyl, substituted heterocyclylsulfonylamino, sulfoxyacylamino, thiocarbamoyl, trifluoromethyl;

$R_4$ is selected from the group consisting of hydrogen, $C_{1-4}$-alkyl, $C_{1-4}$-alkyl-$CO_2H$, and phenyl, wherein the $C_{1-4}$-alkyl, $C_{1-4}$-alkyl-$CO_2H$, and phenyl groups are either unsubstituted or functionalized with one to three substituents selected from the group consisting of halogen, —OH, —OMe, —$NH_2$, $NO_2$, benzyl, and benzyl functionalized with one to three substituents selected from the group consisting of halogen, —OH, —OMe, —$NH_2$, and —$NO_2$;

$R_5$ is selected from the group consisting of —$(CR_1R_2)_n$COOH, —$C(CF_3)_2OH$, —$CONHNHSO_2CF_3$, —$CONHOR_4$, —$CONHSO_2R_4$, —$CONHSO_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR_4$, —$OPO_3H_2$, —$OSO_3H$, —$PO(OH)R_4$, —$PO_3H_2$, —$SO_3H$, —$SO_2NHR_4$, —$SO_3NHCOR_4$, —$SO_3NHCONHCO_2R_4$, and the following:

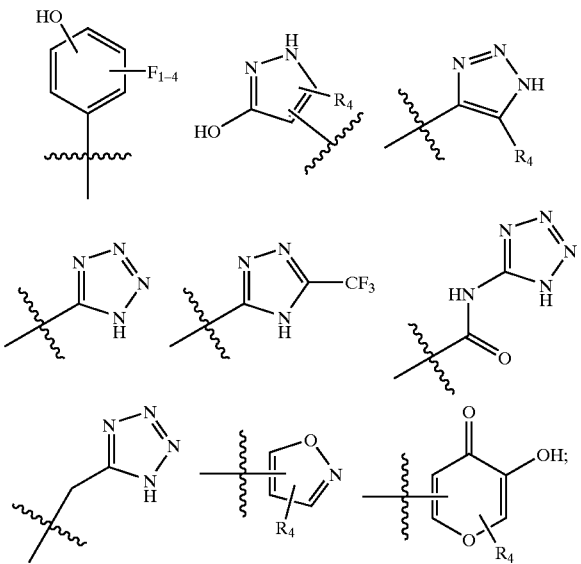

n=0,1,2 or 3;

A is selected from the group consisting of —CH═CH, —$(CH_2)_m$—$(CH_2)_m$, —CH═CH—$CH_2$, and —$CH_2$—CH═CH;

each m is independently selected from 1 or 2;

X is O or S;

Z is selected from the group consisting of a single bond, —O—, —$(CH_2)_n$—, —$O(CH_2)_{1-2}$—, —$CH_2OCH_2$—, —$(CH_2)_{1-2}O$—, and $R_6$ is selected from the group consisting of hydrogen, alkyl, acyl, alkylsufonyl, aralkyl, substituted aralkyl, substituted alkyl, and heterocyclyl; and $R_7$ is selected from the group consisting of:
a) hydrogen;
b) alkyl, alkenyl of not less than 3 carbons, or alkynyl of not less than 3 carbons; wherein said alkyl, alkenyl or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
c) aryl or substituted aryl
d) alkylaryl or alkyl substituted aryl.

2. The compound of claim 1, wherein the compound is in a form selected from the group consisting of an achiral compound, a racemate, an optically active compound, a pure diastereomer, a mixture of diastereomers, and a pharmacologically acceptable addition salt.

3. The compound of claim 1 wherein $R_1$ and $R_2$ are independently selected from the group consisting of
   a) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
   b) aryl or substituted aryl.

4. The compound of claim 3 wherein wherein at least one of $R_1$ and $R_2$ is alkyl.

5. The compound of claim 1 wherein A is $—(CH_2)_m—(CH_2)_m$.

6. The compound of claim 1 wherein $R_7$ is alkyl.

7. The compound of claim 1 wherein Z is a single bond.

8. A compound of formula II:

FORMULA II

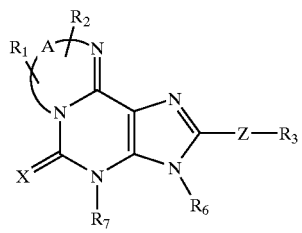

or a pharmacologically acceptable addition salt thereof
   wherein $R_1$ and $R_2$ are independently selected from the group consisting of:
   a) hydrogen;
   b) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
   c) aryl or substituted aryl;
   $R_3$ is a bicyclic, tricyclic or pentacyclic group selected from the group consisting of:

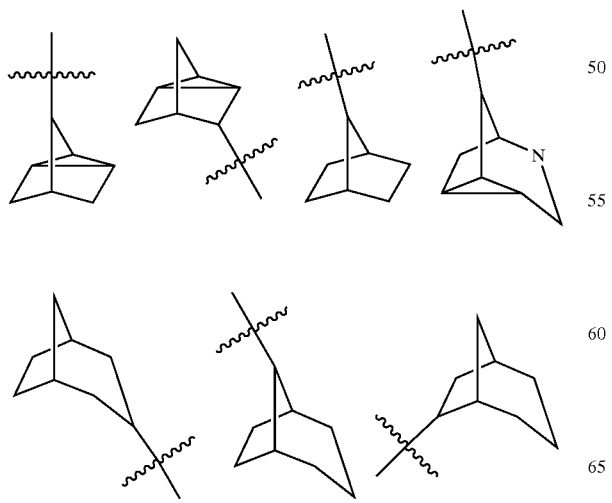

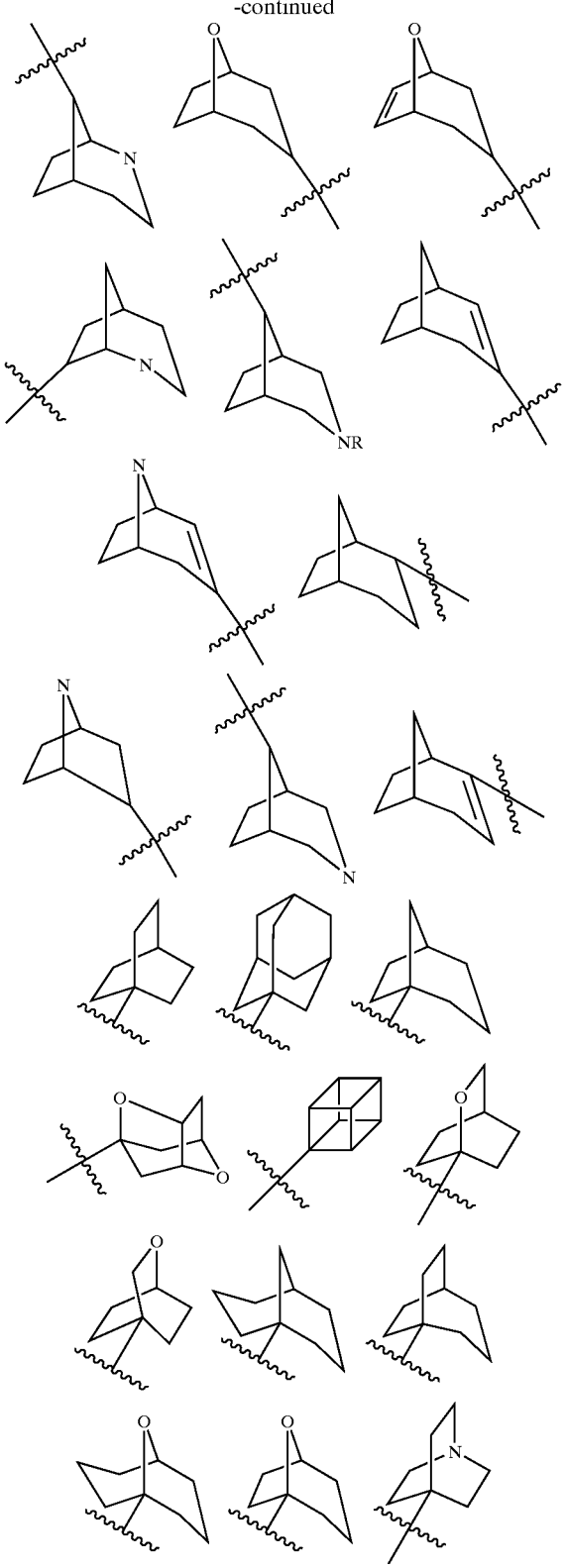

wherein the bicyclic, tricyclic or pentacyclic group is either unsubstituted or functionalized with one or more substituents selected from the group consisting of:
   (i) alkyl, alkenyl and alkynyl; wherein each alkyl, alkenyl or alkynyl group is either unsubstituted or functionalized with one or more substituents selected from the group consisting of (alkoxycarbonyl)aralkylcarbamoyl, (amino)(R$_5$)acylhydrazinylcarbonyl, (amino)(R$_5$)acyloxycarboxy, (hydroxy)(carboalkoxy)alkylcarbamoyl, acyloxy, aldehydo, alkenoxy, alkenylamino, alkenylsulfonylamino, alkoxy, alkoxycarbonyl, alkoxycarbonylamino, alkoxycarbonylaminoacyloxy, alkylamino, alkylcarbamoyl, alkylphosphono, alkylsulfonylanimo, alkysulfonyloxy, amino, aminoacyloxy, aralkoxycarbonyl, aralkoxycarbonylamino, arylheterocyclyl, aryloxy, arylsulfonylamino, arylsulfonyloxy, carbamoyl, cyano, cycloalkylamino, dialkylamino, dialkylphosphono, haloalkylsulfonylamino, halogen, heterocyclyl, heterocyclylcarbamoyl, hydroxy, —R$_5$, R$_5$-alkoxy, R$_5$-alkyl(alkyl)amino, R$_5$-alkylamino, R$_5$-alkylsulfonyl, R$_5$-alkylsulfonylamino, R$_5$-alkylthio, R$_5$-heterocyclylcarbonyl, substituted aralkylamino, substituted arylcarboxyalkoxycarbonyl, substituted heteroarylsulfonylamino, substituted heterocyclyl, substituted heterocyclylsulfonylamino, sulfoxyacylamino, thiocarbamoyl, trifluoromethyl; and (ii) (alkoxycarbonyl)aralkylcarbamoyl, (amino)(R$_5$)acylhydrazinylcarbonyl, (amino)(R$_5$)acyloxycarboxy, (hydroxy)(carboalkoxy)alkylcarbamoyl, acyloxy, aldehydo, alkenoxy, alkenylamino, alkenylsulfonylamino, alkoxy, alkoxycarbonyl, alkoxycarbonylamino, alkoxycarbonylaminoacyloxy, alkylamino, alkylcarbamoyl, alkylphosphono, alkylsulfonylamino, alkylsulfonyloxy, amino, aminoacyloxy, aralkoxycarbonyl, aralkoxycarbonylamino, arylheterocyclyl, aryloxy, arylsulfonylamino, arylsulfonyloxy, carbamoyl, cyano, cycloalkylamino, dialkylamino, dialkylphosphono, haloalkylsulfonylamino, halogen, heterocyclyl, heterocyclylcarbamoyl, hydroxy, —R$_5$, R$_5$-alkoxy, R$_5$-alkyl(alkyl)amino, R$_5$-alkylamino, R$_5$-alkylsulfonyl, R$_5$-alkylsulfonylamino, R$_5$-alkylthio, R$_5$-heterocyclylcarbonyl, substituted aralkylamino, substituted arylcarboxyalkoxycarbonyl, substituted heteroarylsulfonylamino, substituted heterocyclyl, substituted heterocyclylsulfonylamino, sulfoxyacylamino, thiocarbamoyl, trifluoromethyl;

R$_4$ is selected from the group consisting of hydrogen, C$_{1-4}$-alkyl, C$_{1-4}$-alkyl—CO$_2$H, and phenyl, wherein the C$_{1-4}$-alkyl, C$_{1-4}$-alkyl-CO$_2$H, and phenyl groups are either unsubstituted or functionalized with one to three substituents selected from the group consisting of halogen, —OH, —OMe, —NH$_2$, NO$_2$, benzyl, and benzyl functionalized with one to three substituents selected from the group consisting of halogen, —OH, —OMe, —NH$_2$ and —NO$_2$;

R$_5$ is selected from the group consisting of —(CR$_1$R$_2$)$_n$COOH, —C(CF$_3$)$_2$OH, —CONHNHSO$_2$CF$_3$, —CONHOR$_4$, —CONHSO$_2$R$_4$, —CONHSO$_3$NHR$_4$, —C(OH)R$_4$PO$_3$H$_2$, —NHCOCF$_3$, —NHCONHSO$_2$R$_4$, —NHPO$_3$H$_2$, —NHSO$_2$R$_4$, —NHSO$_2$NHCOR$_4$, —OPO$_3$H$_2$, —OSO$_3$H, —PO(OH)R$_4$, —PO$_3$H$_2$, —SO$_3$H, —SO$_2$NHR$_4$, —SO$_3$NHCOR$_4$, —SO$_3$NHCONHCO$_2$R$_4$, and the following:

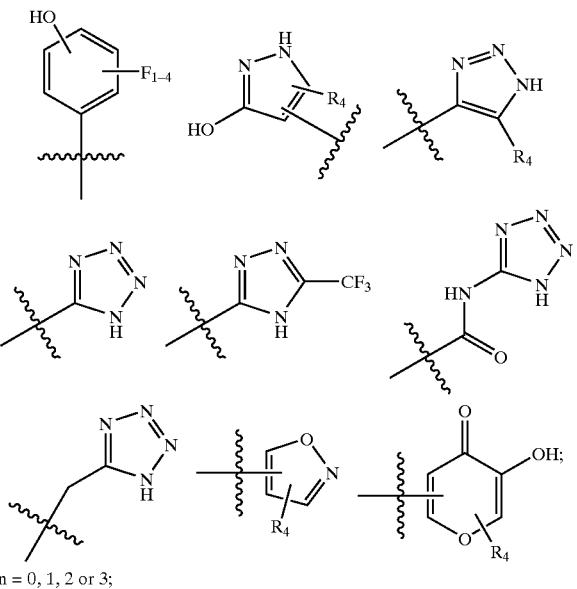

n = 0, 1, 2 or 3;

A is selected from the group consisting of —CH=CH, —(CH$_2$)$_m$—(CH$_2$)$_m$, —CH=CH—CH$_2$, and —CH$_2$—CH=CH;

each m is independently selected from 1 or 2;

X is O or S;

Z is selected from the group consisting of a single bond, —O—, —(CH$_2$)$_n$—, —O(CH$_2$)$_{1-2}$—, —CH$_2$OCH$_2$—, and —(CH$_2$)$_{1-2}$O—;

R$_6$ is selected from the group consisting of hydrogen, alkyl, acyl, alkylsufonyl, aralkyl, substituted aralkyl, substituted alkyl, and heterocyclyl; and R$_7$ is selected from the group consisting of:
  a) hydrogen;
  b) alkyl, alkenyl of not less than 3 carbons, or alkynyl of not less than 3 carbons; wherein said alkyl, alkenyl or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
  c) aryl or substituted aryl
  d) alkylaryl or alkyl substituted aryl.

9. The compound of claim 8, wherein the compound is in a form selected from the group consisting of an achiral compound, a racemate, an optically active compound, a pure diastereomer, a mixture of diastereomers, and a pharmacologically acceptable addition salt.

10. The compound of claim 8 wherein R$_1$ and R$_2$ are independently selected from the group consisting of
  a) alkyl, alkenyl or alkynyl, wherein said alkyl, alkenyl, or alkynyl is either unsubstituted or functionalized with one or more substituents selected from the group consisting of hydroxy, alkoxy, amino, alkylamino, dialkylamino, heterocyclyl, acylamino, alkylsulfonylamino, and heterocyclylcarbonylamino; and
  b) aryl or substituted aryl.

11. The compound of claim 10 wherein at least one of R$_1$ and R$_2$ is alkyl.

12. The compound of claim 8 wherein A is —(CH$_2$)$_m$—(CH$_2$)$_m$.

13. The compound of claim 8 wherein $R_7$ is alkyl.
14. The compound of claim 8 wherein Z is a single bond.
15. The compound according to claim 1 or 8, wherein the compound is selected from the group consisting of:
| Compound | Structure |
|---|---|
| 1 | 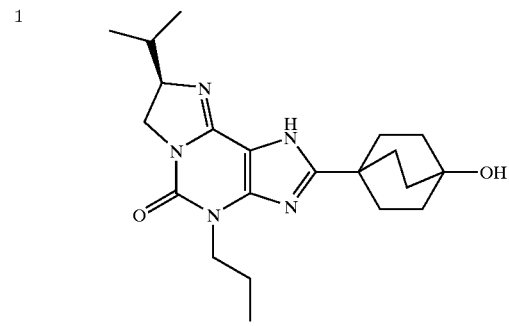 |
| 2 | 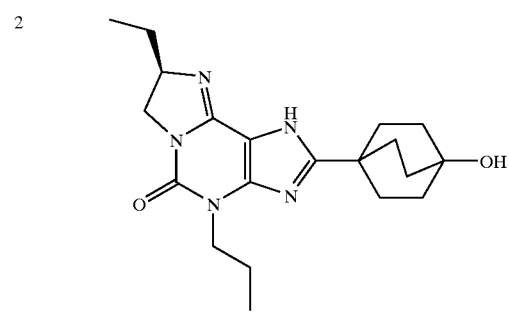 |
| 3 | 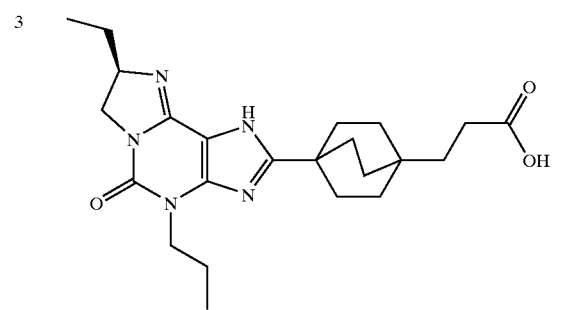 |
| 4 | 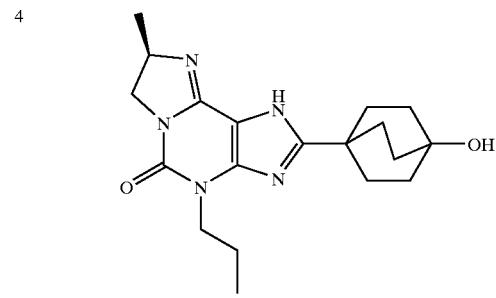 |
-continued
| Compound | Structure |
|---|---|
| 5 | 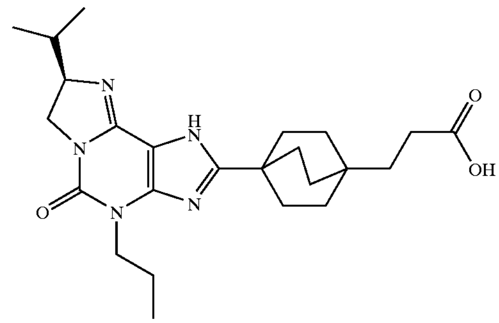 |
| 6 | 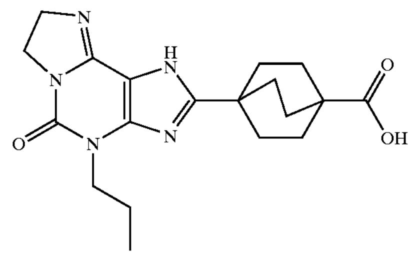 |
| 7 | 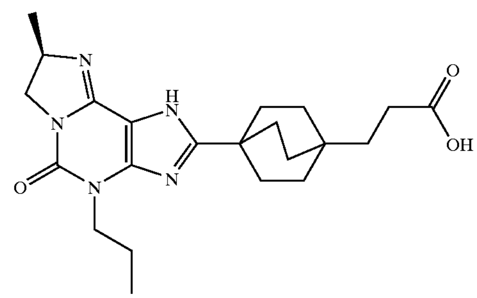 |
| 8 | 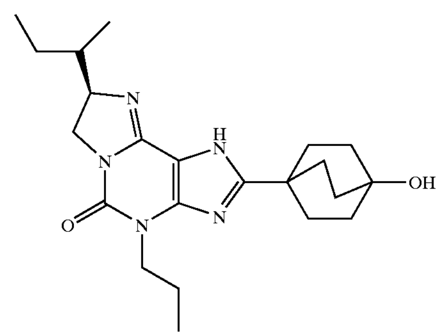 |
| 9 | 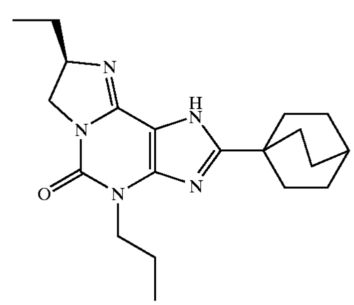 |

-continued
| Compound | Structure |
|---|---|
| 10 | 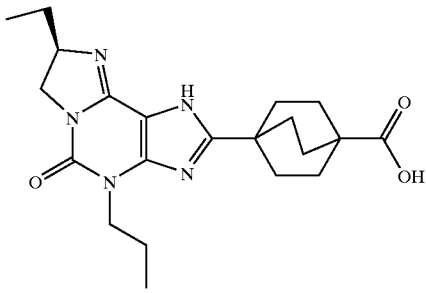 |
| 11 | 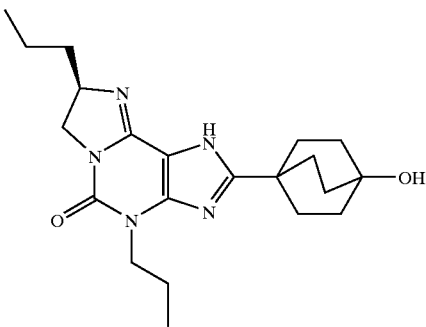 |
| 12 | 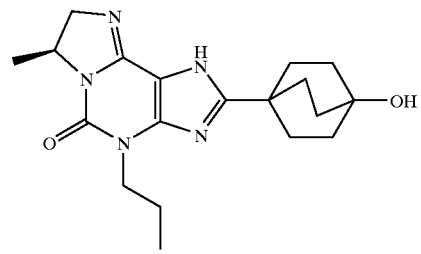 |
| 13 | 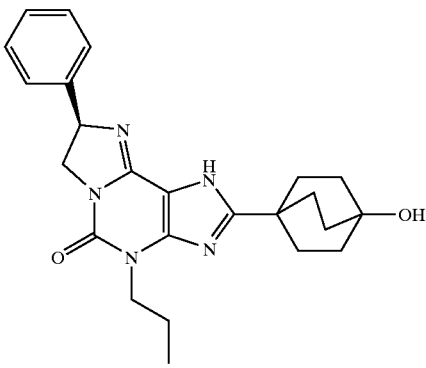 |
| 14 | 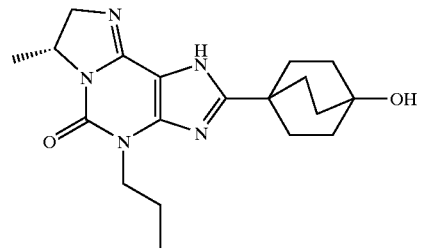 |
-continued
| Compound | Structure |
|---|---|
| 15 | 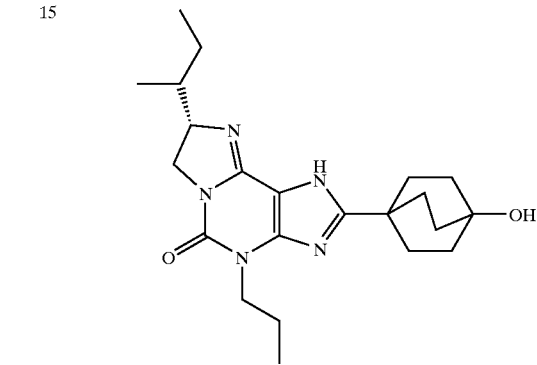 |
| 16 | 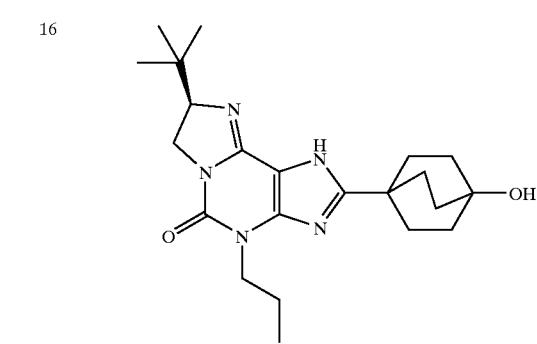 |
| 17 | 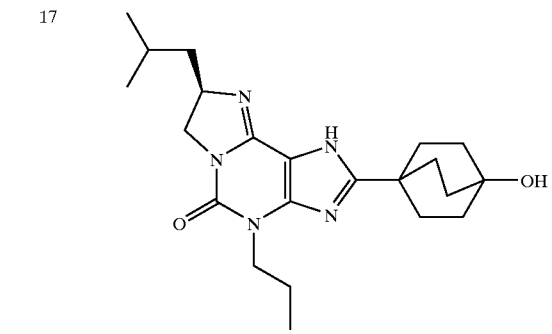 |
| 19 | 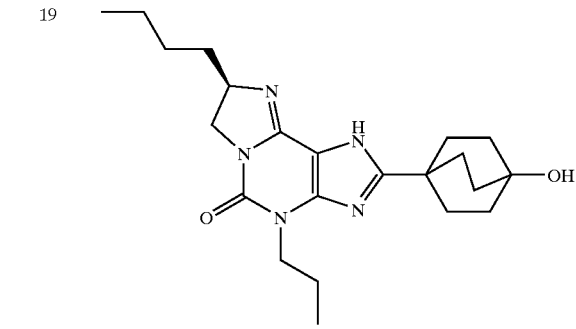 |

-continued
| Compound | Structure |
|---|---|
| 20 | 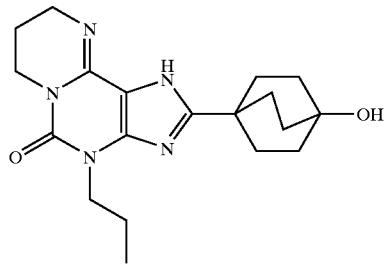 |
| 21 | 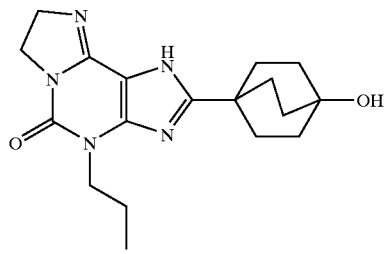 |
| 22 | 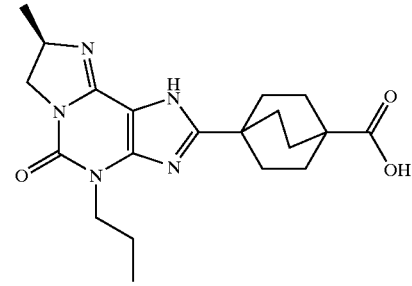 |
| 23 | 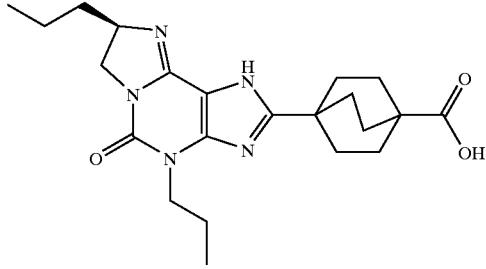 |
| 24 | 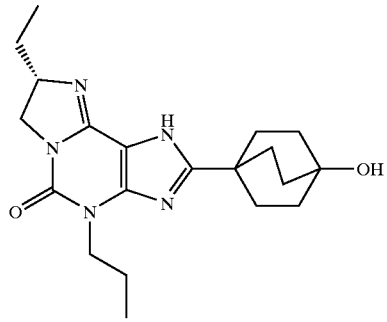 |
-continued
| Compound | Structure |
|---|---|
| 25 | 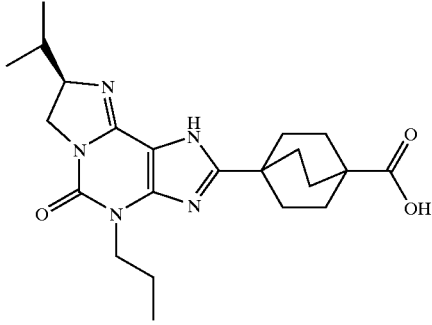 |
| 26 | 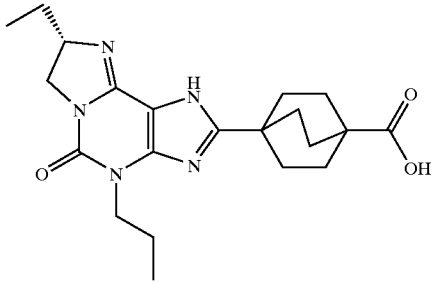 |
| 27 | 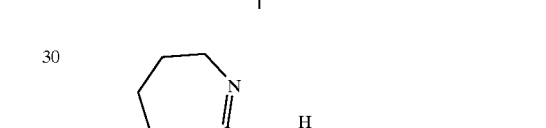 |
| 29 | 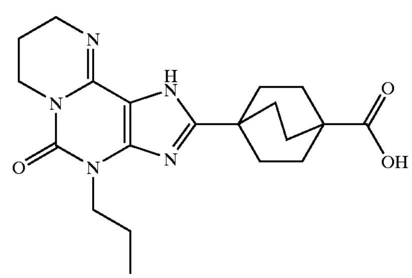 |
| 30 | 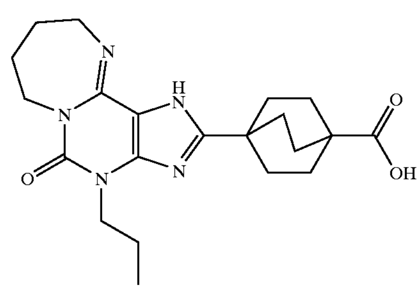 |

-continued

| Compound | Structure |
|---|---|
| 31 | *(chemical structure)* |
| 32 | *(chemical structure)* |

16. The compound according to claim 15, wherein the compound is selected from the group consisting of:

2-(4-Hydroxy-bicyclo[2.2.2]oct-1-yl)-7-isopropyl-4-propyl-1,4,6,7-tetrahydro-1,3,4,5a,8-pentaaza-as-indacen-5-one (compound 1);

7-Ethyl-2-(4-hydroxy-bicyclo[2.2.2]oct-1-yl)-4-propyl-1,4,6,7-tetrahydro-1,3,4,5a,8-pentaaza-as-indacen-5-one (compound 2);

3-[4-(7-Ethyl-5-oxo-4-propyl-4,5,6,7-tetrahydro-1H-1,3,4,5a,8-pentaaza-as-indacen-2-yl)-bicyclo[2.2.2]oct-1-yl]-propionic acid (compound 3);

2-(4-Hydroxy-bicyclo[2.2.2]oct-1-yl)-7-methyl-4-propyl-1,4,6,7-tetrahydro-1,3,4,5a,8-pentaaza-as-indacen-5-one (compound 4); and 3-[4-(7-Isopropyl-5-oxo-4-propyl-4,5,6,7-tetrahydro-1H-1,3,4,5a,8-pentaaza-as-indacen-2-yl)-bicyclo[2.2.2]oct-1-yl]-propionic acid (compound 5).

17. A pharmaceutical composition comprising a pharmaceutically effective amount of a compound according to claim 1 or 8 and a pharmaceutically acceptable carrier, adjuvant or vehicle.

18. A method of treating a patient suffering from a disease or disorder selected from the group consisting of systemic hypertension, renal failure, diabetes, asthma, congestive heart failure, and renal dysfunction comprising administering to said patient a pharmaceutically effective amount of a pharmaceutical composition according to claim 17.

19. The pharmaceutical composition according to claim 17, wherein the composition is formulated for oral, intravenous, intramuscular or subcutaneous administration.

* * * * *

UNITED STATES PATENT AND TRADEMARK OFFICE
CERTIFICATE OF CORRECTION

PATENT NO.    : 6,605,601 B2
DATED         : August 12, 2003
INVENTOR(S)   : Ko-Chung Lin et al.

It is certified that error appears in the above-identified patent and that said Letters Patent is hereby corrected as shown below:

Column 3,
Line 5, change 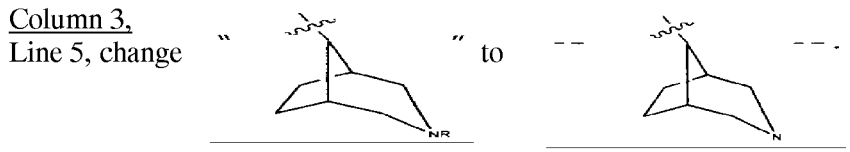 to

Column 5
Line 18, change "CONHS$_2$NHR$_4$" to -- CONHSO$_2$NHR$_4$ --.
Line 55, delete "13" at end of line.

Column 7,
Line 21, change "feature" to -- features --.

Column 13,
Line 39, change "adeno sine" to -- adenosine --.
Line 45, change "failure,;" to -- failure; --.

Column 15,
Line 10, change "including," to -- including --.
Line 36, change "include," to -- include --.

Column 16,
Line 43, change "(compound 24)" to -- (compound 24); --.
Line 57, change "(4.14 g, . 1 . 2 eq)" to -- (4.14 g, 1.2 eq) --.

Column 17,
Line 15, change "teaction" to -- reaction --.

Column 19,
Line 43, change "MeI" to -- MeI --.

Column 21,
Line 35, change "5.6 m" to -- 5.6 mM --.

Column 24,
Line 2, change "A$_1$AdoRs" to -- A$_1$AdoR --.

Column 38,
Line 25, change  to

UNITED STATES PATENT AND TRADEMARK OFFICE
CERTIFICATE OF CORRECTION

PATENT NO. : 6,605,601 B2
DATED : August 12, 2003
INVENTOR(S) : Ko-Chung Lin et al.

It is certified that error appears in the above-identified patent and that said Letters Patent is hereby corrected as shown below:

Column 40,
Line 12, delete "-$SO_3NHCOR_4$, -$SO_3NHCONHCO_2R_4$,".
Line 49, change "alkylsufonyl" to -- alkylsulfonyl --.

Column 41,
Line 12, delete the second occurrence of "wherein".

Column 42,
Line 15, change "  " to --  --.

Column 43
Line 10, change "alkysulfonyloxy" to -- alkylsulfonyloxy --.
Line 16, change "heterocyc lylcarblamoyl" to -- heterocyclylcarbamoyl --.
Line 61, change "-$CONHSO_3NHR_4$" to -- $CONHSO_2NHR_4$ --.
Line 66, delete "-$SO_3NHCOR_4$, -$SO_3NHCONHCO_2R_4$,"

Column 44,
Line 35, change "alkylsufonyl" to -- alkylsulfonyl --.

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,605,601 B2
DATED : August 12, 2003
INVENTOR(S) : Ko-Chung Lin et al.

It is certified that error appears in the above-identified patent and that said Letters Patent is hereby corrected as shown below:

Column 3,
Line 5, change 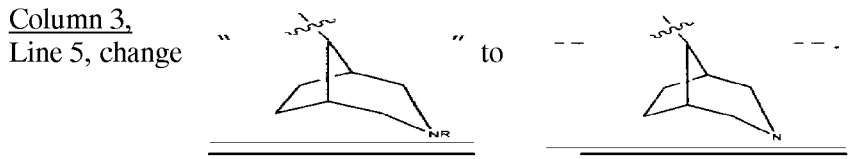 to

Column 5
Line 18, change "CONHS$_2$NHR$_4$" to -- CONHSO$_2$NHR$_4$ --.
Line 55, delete "13" at end of line.

Column 7,
Line 21, change "feature" to -- features --.

Column 13,
Line 39, change "adeno sine" to -- adenosine --.
Line 45, change "failure,;" to -- failure; --.

Column 15,
Line 10, change "including," to -- including --.
Line 36, change "include," to -- include --.

Column 16,
Line 43, change "(compound 24)" to -- (compound 24); --.
Line 57, change "(4.14 g, . 1 . 2 eq)" to -- (4.14 g, 1.2 eq) --.

Column 17,
Line 15, change "teaction" to -- reaction --.

Column 19,
Line 43, change "MeI" to -- MeI --.

Column 21,
Line 35, change "5.6 m" to -- 5.6 mM --.

Column 24,
Line 2, change "A$_1$AdoRs" to -- A$_1$AdoR --.

Column 38,
Line 25, change 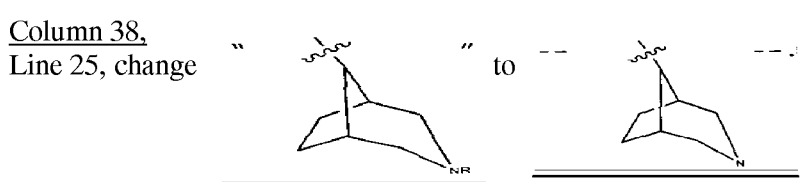 to

UNITED STATES PATENT AND TRADEMARK OFFICE
CERTIFICATE OF CORRECTION

PATENT NO.   : 6,605,601 B2
DATED        : August 12, 2003
INVENTOR(S)  : Ko-Chung Lin et al.

It is certified that error appears in the above-identified patent and that said Letters Patent is hereby corrected as shown below:

Column 40,
Line 12, delete "-SO$_3$NHCOR$_4$, -SO$_3$NHCONHCO$_2$R$_4$,".
Line 49, change "alkylsufonyl" to -- alkylsulfonyl --.

Column 41,
Line 12, delete the second occurrence of "wherein".

Column 42,
Line 15, change "  " to --  --.

Column 43
Line 10, change "alkysulfonyloxy" to -- alkylsulfonyloxy --.
Line 16, change "heterocyc lylcarbamoyl" to -- heterocyclylcarbamoyl --.
Line 61, change "-CONHSO$_3$NHR$_4$" to -- CONHSO$_2$NHR$_4$ --.
Line 66, delete "-SO$_3$NHCOR$_4$, -SO$_3$NHCONHCO$_2$R$_4$,"

Column 44,
Line 35, change "alkylsufonyl" to -- alkylsulfonyl --.

This certificate supersedes Certificate of Correction issued November 9, 2004.

Signed and Sealed this

Third Day of May, 2005

JON W. DUDAS
*Director of the United States Patent and Trademark Office*